| (12) | United States Patent<br>Koivu et al. | (10) Patent No.: US 7,728,192 B2<br>(45) Date of Patent: Jun. 1, 2010 |

(54) PROCESS FOR CONVERTING STORAGE RESERVES OF DICOTYLEDONOUS SEEDS INTO COMPOSITIONS COMPRISING ONE OR MORE GENE PRODUCTS

(76) Inventors: Kimmo Koivu, Riihikallionkuja 8, Itasalmi (FI) FIN-01100; Viktor Kuvshinov, Kurupolku 1, Vantaa (FI) 01280; Anne Kanerva, Riihikallionkuja 8, Itasalmi (FI) FIN-01100; Andrei Anissimov, Tilanhoitajankaari 4 A 26, Helsinki (FI) FIN-00790; Seppo Paavo Kaijalainen, Retkeilijankuja 4 B 21, Helsinki (FI) FIN-00980

( * ) Notice: Subject to any disclaimer, the term of this patent is extended or adjusted under 35 U.S.C. 154(b) by 174 days.

(21) Appl. No.: 11/975,198

(22) Filed: Oct. 18, 2007

(65) Prior Publication Data

US 2008/0222751 A1 Sep. 11, 2008

Related U.S. Application Data

(63) Continuation-in-part of application No. 10/149,121, filed on Jun. 7, 2002, now abandoned.

(51) Int. Cl.
*C12N 15/82* (2006.01)
(52) U.S. Cl. .................. 800/287; 800/278; 800/288

(58) Field of Classification Search ............... None
See application file for complete search history.

(56) References Cited

U.S. PATENT DOCUMENTS 7,473,825 B2 * 1/2009 Takaiwa et al. .......... 800/320.1

OTHER PUBLICATIONS

Lamtham et al. Removal of antibiotic resistance genes from transgenic tobacco plastids. (2000) Nature Biotechnology; vol. 18; pp. 1172-1176.*

* cited by examiner

*Primary Examiner*—Cathy Kingdon Worley
(74) *Attorney, Agent, or Firm*—Dodds and Associates; L. Susanne Somersalo; John H. Dodds

(57) ABSTRACT

The present invention is related to a process based on a source-sink principle, for producing products of interest from crushed or uncrushed germinating dicotyledonous seeds comprising an expression system, which is induced or can be induced during germination. The product is either a seed derived composition comprising one or more gene products. Alternatively, it is a product of interest obtained by placing the composition in contact with a substrate, containing a substance capable of being transformed by the seed derived composition as such, dried or in down-stream processed form.

16 Claims, 15 Drawing Sheets

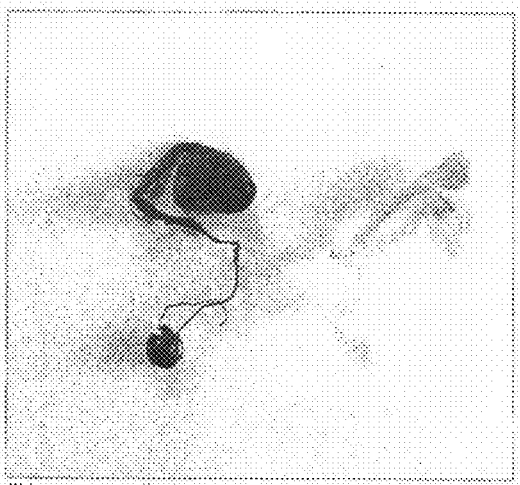
Figure 1A.
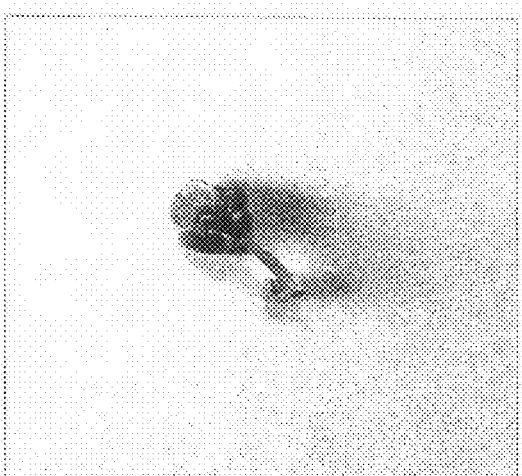
Figure 1B.
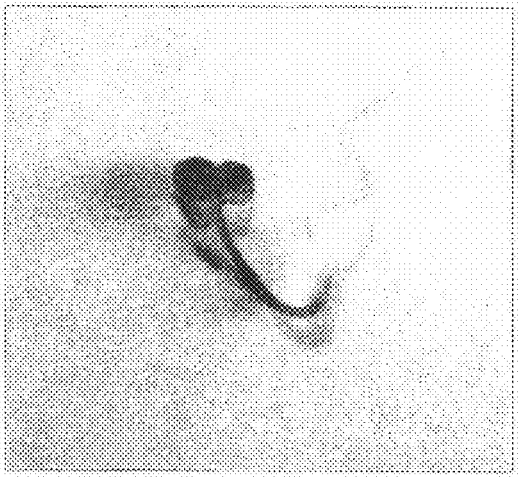
Figure 1C.
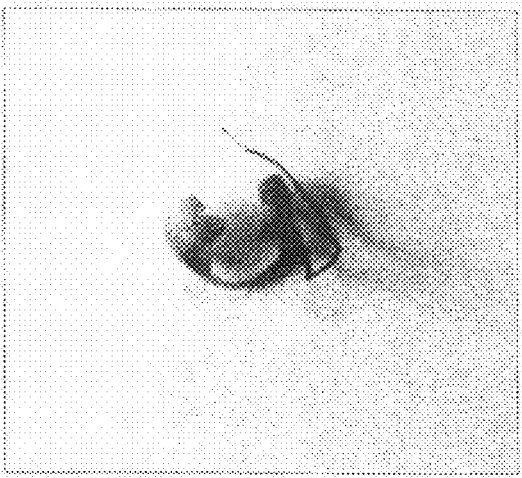
Figure 1D.
Figure 1.

| Period of germination (hours) | HSA mRNA in Rbcs-4-HSA plants, pg/μg total RNA | HSA mRNA in (Rbcs-2-HSA) x2 plants, pg/μg total RNA | Rubisco mRNA in Rbcs-4-HSA plants, pg/μg total RNA |
|---|---|---|---|
| 12 | 0 | 0 | 0 |
| 24 | 0 | 4.1 | 1.38 |
| 36 | 2.51 | 7.5 | 52.9 |
| 48 | 15.65 | 11.9 | 113.24 |
| 60 | 13 | 7.2 | 117.46 |
| 72 | 20.25 | 12.5 | 113.82 |
| 96 | 21.4 | 7.4 | 108.55 |
| 168 | 16.7 | 6.5 | 99.88 |

Fig. 13

| Constructs | GUS activity pM / min$^{-1}$ x mg$^{-1}$ Average value (range) | |
|---|---|---|
| | Camelina | Tobacco |
| RbcS-2-GUS | 1131 (631-1445) | 4531 (1674-7730) |
| RbcS-4-GUS | 1889 (1091-2768) | 1591 (1512-1669) |
| 35Sp-GUS (positive control) | 231 | 1216 |
| Non-transgenic (negative control) | 113 | 219 |

Fig. 14

| Construct | Camelina, mRNA, pg/μg; average value (range) | Tobacco, mRNA, pg/μg; average value (range) |
|---|---|---|
| Rbcs-2-TNFR-Fc-56UTRshort | 0.6 (one sample available) | No samples available |
| Rbcs-2-TNFR-FcKDEL-56UTRshort | No samples available | 1.0 (one sample available) |
| Rbcs-4-TNFR-Fc-56UTRlong | 3.75 (0.5-10) | No samples available |
| Rbcs-4-TNFR-FcKDEL-56UTRlong | 9.7 (6-13) | No samples available |

PROCESS FOR CONVERTING STORAGE RESERVES OF DICOTYLEDONOUS SEEDS INTO COMPOSITIONS COMPRISING ONE OR MORE GENE PRODUCTS

This application is a Continuation-in Part application, of U.S. application Ser. No. 10/149,121 filed Jun. 7, 2002 now abandoned. This application claims priority of U.S. application Ser. No. 11/433,097, which is a divisional application of patent application Ser. No. 10/884,283 now an issued U.S. Pat. No. 7,115,733, which claims priority of U.S. provisional application No. 60/484,707.

SEQUENCE DATA

This application contains sequence data provided on a computer readable diskette and as a paper version. The paper version of the sequence data is identical to the data provided on the diskette.

TECHNICAL FIELD OF THE INVENTION

The present invention is related to a process based on a source-sink principle for converting the storage reserves of transgenic dicotyledonous seeds into a composition comprising one or more gene products of interest. The invention also discloses a germinating seed derived composition comprising at least one gene product in the cotyledon including the seedling or in the medium surrounding the germinating seed or seedling.

BACKGROUND OF THE INVENTION

Due to increased contamination risks, methods for producing therapeutically active mammalian proteins by isolation and purification from mammalian sources have largely been replaced by recombinant DNA technology. Recombinant DNA technology provides new means for producing large amounts of industrially desirable mammalian proteins and a large choice of hosts and expression systems. When mammalian proteins are the desired target proteins, eukaryotic host systems are preferred in order to obtain glycosylated forms of the desired proteins.

Fungi represent the most effective host system for high volume and low cost production of glycosylated proteins. Even if fungi have been successful for producing high amounts of their native proteins, they have not been equally successful in expressing heterologous proteins, such as therapeutic mammalian proteins.

Fungi are used mainly for large-scale production of homologous industrial enzymes, whereas the focus of research is increasingly in finding alternative expression systems for producing glycosylated heterologous proteins. Because glycosylation patterns and folding processes in plant host systems resemble those in mammalian systems, plant host expression systems are by far the most cost-effective of the available systems. The main interest is on production of pharmaceuticals and industrially important enzymes. The production of interferon, enkephalins, epidermal growth factor and human serum albumin in tobacco, and/or potato are mentioned as examples. The expression levels in transgenic plants, however, have been rather low.

In plant expression systems, foreign genes are generally expressed under strong tissue specific plant promoters in developing plant organs. Typical examples are the seed storage protein promoter or the tuber specific patatin promoter in potato tubers. Alternatively, cell or organ cultures and algal cultures are used as well as even more sophisticated systems including plant virus based systems, with the desired gene coupled inside the virus genome and expressed concurrently with viral proteins. The most advanced systems rely on inducible expression and secretion of recombinant protein to the medium.

The U.S. Pat. No. 5,693,506 and U.S. Pat. No. 5,994,628 disclose a production system for producing foreign proteins in germinating monocotyledonous seeds. Recombinant proteins are expressed under a strong amylase promoter in a cell culture or in germinating seed and the protein is secreted into the growth medium or extracted from malt. In a monocotyledonous seed, the storage reserves mainly consist of the starchy endosperm. The protein stores in monocotyledonous are scarce as compared to those in dicotyledonous seeds. In addition, even if the amylase expression is high in specific cells, only a small number of cells in the seed express amylase. These cells are restricted to the scutellum of the embryo and the aleurone layer of the endosperm. There is a great demand to provide more cost effective systems, which would take advantage of the storage reserves of proteins and oils in dicotyledonous seeds. The U.S. Pat. No. 5,543,576 and U.S. Pat. No. 5,714,474 disclose a method in which transgenic seeds are added without any pregermination and in ground form into feed mixtures as additional enzyme sources.

The U.S. Pat. No. 5,670,349 discloses the use of wound inducible HMGR/HMG2 promoters for expressing recombinant proteins in fresh tobacco leaves harvested from the field. Wounding of fresh or stored plant material by excision or crushing triggers a rapid increase in expression. However, the protein content in tobacco leaf is small as compared to that obtainable from a dicotyledonous seed. Furthermore, the storability of fresh leaves is not comparable to that of dry seed in respect of time, space and/or storage costs. The use of fresh plant material, such as leaves harvested from the field is also a major source of microbial contamination, which is a serious problem in fermentation technology.

The patent applications WO 94/11519 and WO 97/32986 disclose methods and plants for producing degradation and conversion products in plants by the aid of a malting process. In said methods, it is suggested that the enzymes are active in glyoxysomes, which catalyze the breakdown of fatty acids into acetyl-CoA. This acetyl-CoA which normally is used to make organic acids that can be exported from the glyoxysomes and used in other metabolic pathways, such as respiration and sucrose synthesis should be replaced with gene encoding enzymes in a pathway leading to polyhydroxyalkanoates useful for the production of biodegradable thermoplastics.

Even if malting process is known and has been used especially for preparing monocotyledonous plants, it is restricted to processing starch. Even if the methods disclosed in the patents WO 94/11519 and WO 97/32986 suggest the use of the storage reserves in dicotyledonous, these methods are still restricted to the use of enzymes and pathways that lead sucrose and energy production and to use of these products from the respiratory pathways for resynthesis.

Even if malting is known and methods for using the respiratory pathways in plants for production of polyhydroxyalkanoates, the use of the storage reserves in dicotyledonous plants for producing proteinaceous products, such as structural proteins and enzymes has not been solved.

There is a great demand for proteinaceous products and because of that it is the main objective of the present invention to solve the problem of converting the storage reserves in dicotyledonous plants into different proteinaceous products, which can be further applied for production of desired products.

The main objective of the present invention is to provide a new, more feasible, cost-effective, environmentally friendly process and production system for producing gene products, especially proteinaceous gene products in the cotyledons of transgenic dicotyledonous seeds.

Another objective of the present invention is to provide a production system for contained use, in which the gene product can be produced in confined conditions and not in the field. This allows the present process to be carried out under almost contaminant-free conditions.

The objectives of the present invention are achieved by harnessing the regulatory sequences of transient proteins accumulating during the initiation of germination for the production of desired gene products.

The characteristics of the present invention are as set out in the claims.

BRIEF DESCRIPTION OF THE DRAWINGS

FIG. 1A shows a germinated transgenic seed expressing the GUS gene. The GUS gene is linked to a soybean heat shock promoter. On the right side an untransformed control seedling is shown.

FIG. 1B shows a germinated transgenic seed expressing the GUS gene. The GUS gene is linked to an endopeptidase promoter.

FIG. 1C shows a germinated transgenic seed expressing the GUS gene. The GUS gene is linked to a salicylate inducible promoter.

FIG. 1D shows a germinated transgenic seed expressing the GUS gene. The GUS gene is linked to a CaMV 35S promoter.

FIG. 13 illustrates HSA mRNA content in germinating seeds of transgenic *Brassica napus* plants at various times.

FIG. 14 A illustrates quantitative GUS-activity data for transgenic *Camelina* and tobacco plants transformed with RbcS-2-GUS or RbcS-4-GUS constructs. Plants transformed with 35Sp-GUS are used as positive controls.

FIG. 15 illustrates Northern blot data, obtained from transgenic *Camelina* and tobacco plants carrying TNFR-constructs. Rbcs-2-TNFR-Fc-56UTRshort contains rbcS-2 (SEQ ID NO:3) promoter, TNFR part (489 nt) (SEQ ID NO:19), linked to the part of IgG1 heavy chain constant region ($C_H2+C_H3$ domains), and terminator from natural rbcS-4 gene (0, 5 kb length). Rbcs-2-TNFR-FcKDEL-56UTRshort is the same construct, but there is also KDEL signal (12 nt) (SEQ ID NO:24) after Fc region (just before STOP codon). Rbcs-4-TNFR-Fc-56UTRlong contains rbcS-4A (SEQ ID NO:1) promoter, TNFR part (SEQ ID NO: 19), linked to the part of IgG1 heavy chain constant region ($C_H2+C_H3$ domains), and terminator from natural rbcS-4 gene (2 kb length). Rbcs-4-TNFR-FcKDEL-56UTRlong is the same as previous construct, but there is also KDEL signal (12 nt) (SEQ ID NO:24) after Fc region (just before STOP codon).

DETAILED DESCRIPTION OF THE INVENTION

Definitions

Figure 2:
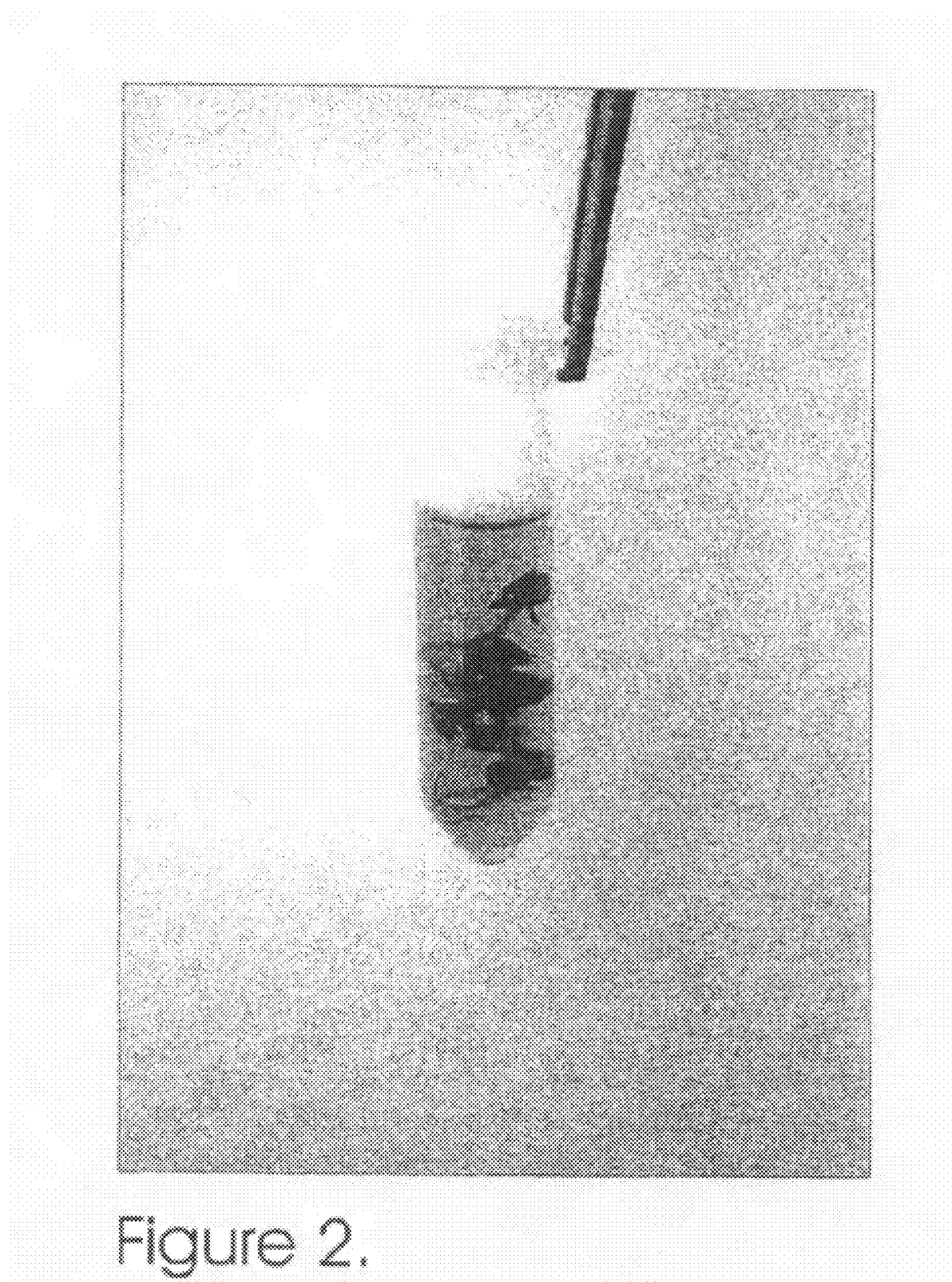
FIG. 2 shows the colorless substrate β-Glucuronide (100 μg/ml) which is enzymatically converted into the blue-colored glucopyranosiduronic acid and aglycone by the GUS enzyme produced by the germinated transgenic seed.

In the present invention, most terms used have the same meaning as they generally have in the field of recombinant DNA techniques, molecular biology and botany, especially in fields related to production of transgenic plants and gene products. Some terms are used, however, in a somewhat different way and are explained in more detail below.

The term "seed plants" means *Spermatophyta* the most developed plants, characterized by complex structures including fully developed organs like root, stem, leaf, flower and the vascular system. Seed plants are divided into two classes, angiosperms and gymnosperms. Angiosperms are further divided into subclasses, i.e. monocotyledonous and dicotyledonous. The embryo of a mature seed of a monocotyledonous plant comprises only one cotyledon, which is reduced to the absorptive scutellum. A dicotyledonous embryo has two cotyledons, which serve as storage organs. The assimilates required for storage deposition in the dicotyledonous cotyledons are translocated from the mother plant through the vascular system to the seed coat and finally to the cotyledon. The seed coat is a maternal tissue and there are no symplastic connections to the embryo. The assimilates pass to the apoplasmic space and are then taken up by the embryo, redistributed symplastically and utilized in the synthesis of the reserves.

The term "dicotyledonous seed" means seed obtainable from a dicotyledonous plant comprising a versatile storage reserve including proteins, lipids and carbohydrates present in the cotyledons in contrast to the storage reserves of monocotyledonous seeds, which consist mainly of carbohydrates and only minor amounts of other compounds. In the present invention, "dicotyledonous seed" means the complete seed or a fragment or a part of the seed obtainable by precrushing the seed, preferably in dry form. The present invention is related to dicotyledonous plants, seeds of monocotyledonous plants cannot be used to achieve the objectives of the present invention.

The most preferred plant genera, which can be applied for producing gene products of interest according to the process of the present invention, include, but are not limited to dicotyledonous plants with high protein or oil content in seeds. Typical examples are the following genera: *Brassicaceae*, *Fabaceae* and *Polygonaceae*. The genus *Brassicaceae* includes for example the following species: *Brassica napus*, *Brassica campestris*, *Camelina sativa*, *Sinapis alba*, *Fabaceae* includes *Lupinus angustifolius*, *Phaseolus vulgaris*, *Glysine max*, *Vicia faba*, *Lens culinaris*, *Pisum sativum*, *Vigna mungo* and *Medicago sativa*. The genus *Polygonaceae* includes the species *Polygonum*. In addition, sunflower, *Helianthus annuus*, is potentially useful because of high oil contents in seeds.

The term "confined system" is used to describe a production system that does not take place in field conditions. A "confined system" may refer for example to closed green house, growth chamber, or to an airlift tank.

The term "source-sink principle" means a production system or production entity, which can be separated into two distinct stages, the accumulation stage in which protein, carbohydrate and lipid reserves are stored into the seed and the mobilization/production stage in which the accumulated reserves normally mobilized for the initiation of growth of the plant are instead mobilized or harnessed for the production of one or more foreign gene products of interest by triggering on the expression system. The accumulation stage comprises cultivation of the transgenic plant with substantially no expression of the gene product in the field whereas the production of the gene products is restricted to the germination in confined conditions. This is achievable by the specificity of expression systems, described in more detail elsewhere in the specification.

The term "surrounding medium" means an aqueous buffer solution either in liquid, semisolid or solid form, which comprises substances capable of initiating, enhancing, delaying or elongating the most favorable stage of the germination. The "surrounding medium" can contain germination inducing, factors up-regulating certain processes and/or factors down-regulating certain other processes as well as external nutrients. The "surrounding medium" can also be a humid space or room.

The term "substrate" means a solid, semisolid or liquid composition or medium, which comprises at least one compound or substance, which can be transformed into another compound or substance with more desirable properties by using the composition of the present invention comprising one or more of the gene products of interest as catalysts.

The term "seed derived composition" means the crude mixture produced by the process of the present invention obtainable from a germinating dicotyledonous seed, which comprises one or more de novo synthesized gene products expressed in the cotyledon of the germinated dicotyledonous seed including the seedling or secreted into the medium surrounding the germinating seed or seedling. The "seed derived composition" can be used as such, or by placing it in contact with the substrate. Naturally, the seed derived composition can be dried and/or treated with applicable down-stream processing methods as well as isolated and/or purified before use. Alternatively, the substrate is a reagent comprising one or more compounds capable of modifying one or more of the gene products in the composition. For example substituents may be added or the folding patterns of the gene product may be modified or fragments or parts removed or added in order to get a more stable product. The "seed derived composition" can also be formulated, i.e. provided with suitable additives, such as granulation improving agents, fillers, lubricants, etc. The germinated seed-derived composition of the present invention can also be added into animal fodder to improve the digestive properties of the fodder.

The term "substantially sterile source-sink production system" means that the dicotyledonous seed can be surface sterilized with methods such as radiation or chemical sterilization. The germination can be carried out in or on a pre-sterilized surrounding medium, using methods applied in aseptic working and/or when working in sterile or super clean conditions. Because the whole production can be performed in sterile conditions, the main causes of seed being killed or not germinating, i.e. fungal or bacterial contamination of seed, can be avoided. Furthermore, the end-product is also substantially contaminant-free and not prone to degradation by contaminants having proteolytic activities. Thus, the production system is also especially suitable for producing pharmaceutical products, which require high hygienic standards.

The term "initiating the germination of the transgenic dicotyledonous seed" means providing conditions favorable for germination. Optionally, it includes storing, drying, sterilizing, adding water, supplementing the seed with inducing or up- and/or down-regulating factors as well as external nutrition. The supplements include both physical and chemical means. External nutrition comprises for example N- and/or C-sources, vitamins, minerals, trace elements, etc. Growth factors, germination-triggering factors, inducers, factors capable of up-regulating some and down-regulating other processes during the de novo synthesis, include for example plant hormones, such as auxin and cytokinin. The physical means includes for example a flash of light or illumination for a longer time, as well as sterilization and/or heating.

The term "expression system" means a DNA construct comprising one or more DNA sequence encoding one or more gene products of interest, operably linked with expression regulating sequences, such as enhancers, promoters and/or terminators. The expression system is preferably such that it is induced or can be induced during germination of the seed, but is substantially silent or can be silenced when the dicotyledonous plant is multiplied and cultivated in field conditions. Preferably, the expression regulating sequences comprise a promoter, which can be called a "camera obscura" promoter, i.e. a promoter that is triggered on or activated during germination, when the seed is kept in non-illuminated conditions in a dark room. This does not preclude the use of illumination or light. On the contrary subjecting the source-sink production system to a flash of light may increase the production of the gene product of interest by inducing and enhancing the activity of the specific promoters.

The expression systems take advantage of such expression regulating sequences, which are especially active in de novo synthesis of transient proteins, which accumulate in the cotyledon during the initiation of the germination. Said inducible expression system comprises inducible regulatory sequences selected from the regulatory sequences of the genes encoding transient proteins which are de novo synthesized during the initiation of germination and accumulating in the cotyledons and endosperm of the plant.

Said expression systems can be prepared by selecting suitable regulatory sequences. The selection method comprises the steps of:

(a) isolating total RNA from cotyledons and/or leaves of dicotyledonous plant;

(b) preparing cDNA from said isolated RNA by amplifying said RNA with one plant specific primer and a primer specific for a protein which is de novo synthesized during the initiation of germination and accumulating in the cotyledons and endosperm of the plant;

(c) collecting and plating the cDNA comprising clones;

(d) comparing the results with clones obtained from leave derived RNA; and (e) recovering the clones comprising the cDNA showing an increased activity in germinating dicotyledonous seeds.

The term "gene product" in the present invention means proteins, polypeptides, including both structural proteins and/or enzymes. Usually, the "gene product" is a peptide, comprising at least two amino acids linked together by a peptide bond. Peptides comprising 2-10 amino acids are called oligopeptides, whereas peptides comprising more than 10 amino acids are called polypeptides. A polypeptide may be a polyamino acid chain, such as a polylysine chain consisting solely of lysine molecules, but it can also be a protein, a protein complex, a part, or a fragment of the protein.

As said in the previous paragraph the term "gene product" can also mean nucleotide-based products, such as mRNA. Also included in the term are other desired biochemicals, compounds or substances, which are obtainable for example by biotransformation processes, in which one or more of the gene products present in the seed derived compositions of the present invention act as catalyzators when placed in contact with a substrate comprising the compound or substance which can be transformed to the desired product or transforms the gene product in desired manner.

Alternatively, "derivatives of the gene products" are obtainable by transformation processes, in which one or more of the original "gene products" of the present invention are modified by allowing a reagent present in the substrate to modify it. The gene products can be made more stable or more active by changing their secondary and/or tertiary structures e.g. by refolding or unfolding the amino acid chain, removing or adding fragments complexing, or adding structures or substituents to said gene products. Such "derivatives of the gene products" are also included within the term "gene products" of the present invention. Usually, the gene products produced by the process of the present invention are heterologous foreign proteins. This means that the "gene product" is not produced by the wild type plant. In other words, it is not native to the host plant. Naturally, the native seed products can be produced using the process of the present invention. It is especially useful to increase the production of certain pharmaceutically useful native homologous plant-derived products.

The term "recovering with or without down-stream processing the gene product expressed by the germinating transgenic dicotyledonous seed" means that the cotyledons including the seedlings can be recovered as such by separating them from the surrounding liquid medium with or without any down-stream processing. Alternatively, the surrounding medium is recovered as such. The storability of the "seed-derived composition" can be improved by drying, extracting, filtering, crushing, etc. Many of these means are simultaneously used for stopping the germination. Heating, drying, crushing, separating, extracting, pressing and filtering are usually applied to stop the germination before the rate of de novo synthesis declines and/or the concentration of the desired gene products goes down. The stopping is of importance, since the germination when allowed to continue too long, start to reuse de novo synthesized desired proteins for production of other substances needed by the nascent plant.

GENERAL DESCRIPTION OF THE INVENTION

The goal of the present invention is to develop a novel process based on a source-sink production system for producing gene products in dicotyledonous seeds. The production system comprises two distinct stages. The first stage is taking advantage of the versatile renewable resources of raw material, such as protein and oil, which are accumulating in the storage reserves of the dicotyledonous plant during cultivation and which can be optionally harvested in form of seeds. The second stage comprises mobilization of the storage reserves in germinating transgenic seed for production of one or more gene products by de novo synthesis of the desired gene product. The second stage may comprise addition of supplements, such as nutritional factors and providing physical and/or chemical means as well as genetic engineering for inducing germination and up- and/or down-regulating the de novo synthesis including transcription, expression and/or secretion.

Structure and Storage Compounds of Dicotyledonous Seeds

The seeds of dicotyledonous plants have two cotyledons, or seed leaves, which are part of the embryo. The cotyledons usually are the main storage tissue. During development in the field, seeds gradually accumulate storage oils, proteins and carbohydrates. Table 1 below, shows percentages of main seed storage compounds in different crop species, including both monocotyledonous as well as dicotyledonous species.

TABLE 1

Percentages of main seed storage compounds in different crop species

| Species | Oil | Protein | Carbohydrate |
|---|---|---|---|
| Brassica rapa | 45-48% | 22-24% | 18-20% |
| Glycine max | 18-20% | 38-40% | 22-27% |
| Medicago sativa | 8-9% | 38-40% | 40% |
| Hordeum vulgare | 3% | 12% | 76% |
| Zea mays | 4% | 8% | 74% |

The cotyledons make up about 90% of the mass of a rapeseed, filling the seed coat and forming a hemisphere around the embryonic axis. The total protein content of rapeseed seed is 22-25% depending on cultivar, growing conditions and crop management. The major rapeseed storage proteins are a 12S type globulin, called cruciferin, which makes up to 60% of the total protein, and 2S type albumin called napin, which make up to 20% of the total protein. Both of these proteins are formed in embryonic cells and stored in specialized vacuoles, known as protein bodies.

In its first stage, the present invention takes advantage of the versatile storage reserves comprising proteins, oils and/or carbohydrates, present in dicotyledonous seeds, but lacking from monocotyledonous seeds. In seeds of monocotyledonous plants, the storage reserves mostly comprise two related forms of starch, amylose and amylopectin. Starch is mobilized by amylases during germination and subsequent growth of the nascent seedling. Resulting sucrose is used as a source of energy and carbon compounds, but the raw material for de novo synthesis, especially of proteins, is much scarcer than in dicotyledonous seeds. Therefore, the storage proteins of dicotyledonous seeds make the germinated seeds into an incomparably excellent source-sink production system according to this disclosure.

In the present invention, transgenic dicotyledonous seeds are harvested for example from the field or green house, transported and stored as usual. The viability of stored seeds can be maintained for long periods, usually up to several years. The temperature and seed moisture content are the major factors in determining seed viability during storage. Generally, seeds are stored at temperatures between 0-5° C. The normal moisture content of stored seed is 4-10%. If the moisture content is less than 20%, seed respires and heat is generated. If ventilation conditions are poor, the heat generated can kill the seed. If the moisture content is over 20%, it can result in deterioration of the seed by microbial growth.

Maturation drying is a normal event in seed development during which seed passes to a metabolically quiescent state. However, seeds of many species may germinate without desiccation. Tomato seeds for example, can germinate when taken from ripening fruit and placed in water. In several other species including *Brassica campestris*, starch content rapidly decreases and the concentration of certain sugars and oligosaccharides increases during desiccation of seeds. Also certain hydrophilic proteins are expressed strongly in desiccating seed. They have the ability to attract water and they are thought to play an important role in the protection against harmful effects of desiccation. Mature dry seed may maintain germination ability and be stored from days to many years. Thus, the crude non-formulated raw material of this invention, the dicotyledonous seeds, can be stably stored up to several years.

Seed Germination

The second stage of the process of the present invention comprises germination of the seeds. In this stage the raw material accumulated during cultivation in the storage reserves of the dicotyledonous seed is mobilized for production of the desired gene products. The up scaling time for germination is fast and the costs low. The production volume is practically unlimited as the raw material is obtainable from renewable resources and the energy input required is obtained from the sun.

In the present invention, germination means the developmental event that begins with water-uptake by the dicotyledonous seed and increased respiration and macromolecular syntheses, storage reserve mobilization and subcellular structural changes. Seed germination occurs rapidly (in oilseed rape it takes 6-8 hours) and it is defined as the emergence of the radicle, the embryonic root of the seed, through the seed coat. The first phase of germination is characterized by rapid water uptake. Seed imbibes usually no more than two or three times the dry seed weight. Germination is generally completed with the radicle extension, which occurs by cell expansion without cell division. In the present invention, germination includes also the growth phase after the start of the elongation of the embryonic axis. After a plateau phase when germination is completed, more water is imbibed. Protein synthesis, using newly synthesized RNAs, begins at the plateau phase within hours after initial water uptake. Enzymes needed for the mobilization of storage reserves are synthesized at the post-germination stage. These enzymes break down the seed insoluble high-molecular-weight compounds into soluble, easily transportable, low-molecular-weight molecules. Several different types of proteases hydrolyze intact storage proteins first into large fragments and then into smaller peptides and amino acids within the protein body. The peptides are transported to the cytosol where other enzymes, e.g. aminopeptidases, carboxypeptidase, dipeptidase and tripeptidase, cleave them and eventually form a pool of free amino acids. The amino acid composition of storage proteins differs from that of the complete sprout. At least in the case of oils seed rape, alfalfa and *Camelina sativa*, amino acids in the sprout are used mainly either directly or indirectly for the synthesis of the Rubisco proteins.

When seed germinates in the nature or in the field, it uses the reserves of the cotyledon to start the physiological activity generally after a quiet stage as dry seed. Vital functions increase rapidly including gene expression. Significant amounts of amino acids and other biological compounds are liberated from the cotyledon storage reserves during the germination and are subsequently bound during the growth of the seedling.

Usually the first group of proteinases appearing during germination are SH-dependent proteinases that act on the insoluble native storage proteins. In the *Vigna mungo* synthesis of SH-dependent proteinase in the cotyledon is initiated immediately after imbibition and it increases until day 4 after which it decreases (Okamoto, T. & Minamikawa, T., J. Plant Physiol., 152(6): 675-682, 1998). The short chain peptides resulting from endopeptidase activity are cleaved from the native proteins, which in turn increases their susceptibility to other proteinases.

A second group of proteinases are inactive against native storage proteins, but hydrolyze short chain peptides to oligopeptides. At the same time also carboxypeptidases are activated and amino acids are released from peptides. This proteolysis happens in the protein body from which the oligopeptides and amino acids are released in the cytosol, where oligopeptides are degraded further into amino acids by amino- and di- or tri-peptidases. Liberated amino acids from the storage organs are further metabolized to the major transported form of amino acids, asparagine and glutamine. Storage proteins represent an amino acid source for de novo synthesized proteins during germination.

According to this invention, the stored reserves in germinating dicotyledonous seeds, which include liberated amino acids and other biochemical substrates, comprise a renewable raw material source entity; whereas expression of the desired transgene by the transcription regulation, functioning in the cotyledon during germination and subsequent seedling growth, forms the production (sink) entity. Thus, the present invention is related to a production system comprising two entities, the source and the sink, i.e. two separate stages: a raw material accumulation stage and a production stage. In the latter, the raw material source is used for de novo synthesis of the gene products and their derivatives or products modified by the gene product from the raw material source obtained in the first stage of the production system.

Storage proteins are generally coded by multigene families. A common feature for the luminal endoplasmic reticulum proteins of eukaryotes is a conserved carboxy-terminal tetrapeptide KDEL, which serves as the ER-retention signal and is always found at the extreme carboxyl terminus. There is no evidence that conservation of more than four terminal amino acids would be needed, although it has been claimed that composition of acidic residues among the terminal 20 amino acids might have some importance for efficient retention. The suggested mechanism of retention is most likely receptor-mediated and involves binding of the KDEL-signal to the membrane receptor and fast return of the signal-receptor complex in the ER, if it is released as a vesicle.

Genetically modified proteins are not always found in their natural cellular compartments. For example high-Met phaseolin expressed in transgenic tobacco is found only in the ER (endoplastic reticulum), Golgi cisternae and Golgi vesicles. Normally phaseolin accumulates in the matrix of protein storage vacuoles of developing tobacco seeds. High-met phaseolin is degraded either in Golgi vesicles or just after entering the protein storage vacuoles. High-level accumulation of *Vicia faba* seed storage protein vicilin with additional carboxy-terminal KDEL-sequence has been reported with tobacco and alfalfa Modified gene constructs fused with cauliflower mosaic virus 35S-promoter and protein are accumulated in (ER) of the leaves of transgenic plants. Accordingly, it seems feasible, that when genetically modified storage proteins are produced, retention in the ER could prevent the degradation and that a DNA construct with cauliflower mosaic virus 35S-promoter could be applied in the present invention.

Cruciferin is a hexamere of six subunits each containing one chain coded by a single gene. For example in *Brassica napus* cruciferin genes share approximately 60% homology between the members. Napin is the second most prominent seed protein in *Brassica napus*. Like cruciferin subunits, napin is a single-gene product composed of two different polypeptide chains linked together with disulfide bridges. Both cruciferin and napin are synthesized at the membrane of ER as precursors containing the ER-targeting signal.

Proteins enter the ER in an unfolded state and the signal sequence is cleaved off soon after the entry. In recent years, it has become clear that not all of the proteins entering the ER are further processed and packed into vacuoles. ER also contains a great number of proteins that remain in the lumen and aid the initial steps in the maturation of secretory proteins. Many of these proteins have been characterized also in mammalian systems, suggesting that the glycosylation of gene products, especially proteins are similar in mammals as well as in plants. In plants, it has been shown that for example the auxin-binding protein is retained in the ER.

Germination can be initiated with surface sterilized seeds by incubating seeds in water or water supplemented with compounds beneficial for the production of a desired gene product. According to this invention gene expression to produce the desired gene product is activated during the germination. To initiate germination, seeds are first hydrated to a moisture content of 40-50% by steeping in water tanks where temperature is adjusted according to the type of seed and the aeration is organized by compressed air. After imbibition, seeds are transferred to germinate usually in 100% moisture chambers. Typically, the temperature is between 10-30° C. and time ranges from 2 to 10 days, preferably 3 to 6 days, most preferably 4 to 5 days.

In the present invention, the germinating dicotyledonous seed comprises a transgenic cotyledon, i.e. cotyledons of dicotyledonous plants being stably transformed with a DNA sequence encoding the desired gene product. Cotyledons are a part of the embryo and they serve as a storage organ. Physiological structure and cell type diversity is relatively simple in the cotyledon. Mobilization of major stored cotyledon reserves begins after germination. In cotyledons the three major forms of storage materials, proteins, oil and carbohydrates are enzymatically converted to a transportable form during seedling growth. Storage proteins are cleaved gradually by a series of proteinases expressed in cotyledon cells. Proteinases are synthesized de novo by structural genes regulated with promoter region functioning in cotyledon.

During germination and subsequent growth of the nascent seedling, storage lipid mobilization is initiated by lipolysis in oil bodies that yields glycerol and free fatty acids from triacylglycerol. In seed storage cell glycerol and free fatty acids are converted to sucrose in complex reactions including dozens of enzymes and at least glyoxysome and mithocondrion organelles. Sucrose is translocated to the vacuole or embryo.

According to this disclosure, in the mobilization/production stage the accumulated protein, carbohydrate and lipid reserves are used as a source of starting material and converted into the commercially interesting products instead of the normal proteins produced to form the plant. The mobilization is started by adding to the seeds a surrounding liquid, semi-solid or solid medium, comprising water, which is supplemented with optional physical or chemical means including nutrition, germination inducing factors as well as factors capable of up- and/or down regulating certain steps in the production (transcription, expression and/or secretion). This mobilization initiates the germination and the production is going on until the emergence of green leaves.

The present invention describes a system that uses dry seed as raw material. Expression of the gene of interest in the transgenic plants carrying an expression system according to this invention is only limited in the field, and the expression is mainly carried out environmentally safely in regulated conditions in a factory instead of field conditions. According to this disclosure, sterilization can be performed by treatment with chemicals like hypochlorite, hydrogen peroxide or with other desinfective compounds. Since dicotyledonous seeds have a smooth surface in contrast to the wrinkled surface texture of monocotyledonous seeds, sterilization of dicotyledonous seeds is much more effective. Consequently, the production of the desired foreign or native gene product(s) can be carried out under sterile conditions, which is a great advantage especially when the target gene product is a therapeutically active protein. Sterile conditions are advantageous also because the microbial degradation of the end product is avoided according to this invention.

The gene product may be recovered substantially contaminant-free, either as a dried plant seed derived composition, comprising one or more gene products accumulated during the germination of the transgenic dicotyledonous seed, and preferably recovered at the point of maximal accumulation by breaking the germination process. The gene product can be recovered as a down-stream processable composition of germinated dicotyledonous seeds or in a storage-stable form. The composition comprises for example proteins, enzymes, peptides, hormones, growth factors, vaccines, amino acids, vitamins and/or antibiotics.

The present invention uses an engineered gene expression system to drive the synthesis to the production of the desired gene product(s) and uses the amino acids, carbon compounds and other gene products liberated during initiation of germination as a raw material source for the de novo synthesis of a transgene product. The natural or native gene products, e.g. proteinases, lipases, amylases, etc. formed in the germinating seeds may be used as substrates for the transgenic enzyme or to form desired biochemicals.

In the present invention the goal is to provide a transgenic plant harboring at least one expression system, comprising at least one DNA sequence encoding at least one desired gene product functionally combined with expression regulating sequences, which are induced or can be induced during germination and are substantially silent or can be silenced when a transgenic dicotyledonous plant is grown in field conditions. Promoters, active in dark (non-illuminated conditions), herein so called camera obscura promoters, including the more or less light independent Rubisco-promoters are useful in the expression system of the present invention.

The present invention provides possibilities to produce different desired gene products, but also other non-gene biochemicals. The transgene expressed during germination produces the first gene product, RNA, from which other RNA-products are obtainable as such or after transformation. Usually the RNA-stage is transient and the gene product recovered is a proteinaceous product. There are principally two kinds of protein products, enzymes and non-enzyme products, which often are structural proteins, vaccines, hormones, etc. The enzymes are capable of modifying an endocellular substrate obtainable from the plant, which is transformed to the desired biochemical compound. Alternatively, an extracellular substrate is added which can be transformed to give another biochemical compound. Subsequently, the protein, whether it is an enzymatically or a non-enzymatically active protein, can be placed in contact with a reagent in which case a derivative of the protein is obtained.

In the present invention, heterologous foreign genes or DNA sequences are designed for optimal expression in germinating cotyledons of a dicotyledonous plant. Sequence characteristics between plant genes and heterologous genes are checked in order to express the foreign transgenic genes from heterologous sources. In plants, it is beneficial to compare the structure of these genes with known plant genes. Pioneering work in this field has been done with *Bacillus thuringiensis* endotoxin genes (cry). Several modifications have to be made in the original gene sequence in order to enhance expression of AT rich cry genes in plants.

A preferred transcriptional start sequence in plants is AACA ATG G (very conservative positions of nucleotides are shown in bold). Of the stop codons TGA, TAG and TAA, the first one has a slight preference and TAA is sparingly used in monocotyledonous. Codons in the gene sequence can be converted to appropriate ones in plants according to the codon usage tables. The converted DNA sequence should be examined for the presence of putative sites decreasing expression in plants. The putative polyadenylation signal sequences in plants usually are AATAAA, AATAAT and their variations: AACCAA, ATATAA, AATCAA, ATACTA, ATAAAA, ATGAAA, AAGCAT, ATTAAT, ATACAT and AAAATA (the most conservative of the A nucleotides are marked by bold). Putative splicing sites excluded from the gene sequence were $CAN_{7-9}$ AGTNNA. Additionally, the DNA sequence should be devoid of ATTTA sequence, which is a putative mRNA degradation element.

The transcription terminator sequences are obtainable from different genes expressed in the seed or other plant genes, for example from the Rubisco gene. Terminators from different bacteria, for example from *Agrobacterium* can be used as well as the nos gene or the ocs gene. The nos gene encodes nopaline synthase and the ocs gene encodes octopine synthase.

RNA polymerase II transcribes protein coding genes in plants in substantially the same way as in other eukaryotic organisms. At the general level, very similar regulation elements can be found in transcription initiation regions (promoter) in eukaryotic cells. TATA box is located 25-40 nucleotides upstream of the transcription initiation site and translation initiation codon, ATG, is located 40-80 nucleotides downstream of the transcription initiation site. In mature mRNA an open reading frame follows the ATG codon and ends with one of three stop codons, UGA, UAG or UAA.

Promoters from variable sources can be used for transgene expression in plants. Many of them are from *Agrobacterium* ssp. and from plant viruses like constitutively expressed *Agrobacterium nos* promoter and cauliflower mosaic virus 35S promoter. Tissue specific promoters are useful for applications where expression in specific tissues is needed. Tissue specific promoters are usually also developmentally controlled so that they are active only at a certain developmental stage of tissue. In the present invention, it is desirable that the promoter is germinating seed specific.

Rubisco Synthesis

Rubisco (ribulose-1,5-bisphosphate carboxylase/oxygenase) represents up to 50% of total protein in germinating cotyledon. It is the most abundant plant protein that catalyzes reactions, where the $CO_2$ molecule condenses with ribulose-1,5-bisphosphate to form two molecules of 3-phosphoglycerate. Rubisco is located on the stromal surface of thylakoid membranes. The enzyme consists of eight large subunits, encoded by the chloroplast genome, and eight small subunit. The small subunit is encoded by a nuclear multigene family (rbcS genes). The small subunit is synthesized on cytoplasmic polysomes as a precursor protein. It is transported into the plastids and processed prior to the assembly of a holoenzyme. RbcS gene expression is tissue and developmental stage specific and is controlled by light by the phytochrome system.

In the present invention, the most preferred gene product or protein production system uses a promoter of Rubisco small subunit gene. Rubisco small subunit gene promoters can be isolated from cotyledons of *Brassica campestris* grown in dark (*camera obscura*) or non-illuminated conditions. This kind of promoter can produce foreign proteins at a very high level. Our work has shown that about 50% of all de novo synthesized proteins in the dark germinating cotyledons of *B. campestris* are small and large subunit proteins of Rubisco. The mRNA level of the native RbcS gene transcript is as high as 500 pg per µg total RNA in germinating seeds. Maximal expression is reached about 60 hours after the start of imbibition. Similar results have been shown with mRNA levels of natural RbcS gene transcripts from *Brassica napus* (Fiebig, C., et al., Bot. Acta 103 (3): 258-265, 1990). Germinating seed can be illuminated with visible light for a shorter or longer time in order to increase expression. Mono-, di- or oligosaccharides, preferably sucrose or glucose can be added to repress the natural rbcS promoter activity. If sucrose responsive element is removed from transgene promoter it will not be repressed by sucrose. When less Rubisco enzyme is produced more free amino acids remain for the transgene expression. In addition, antisense technologies may be used to down-regulate endogenous rbcS gene expression: by expressing antisense rbcS gene in germinating seed.

An advantageous transgenic cotyledon for production of proteins comprises a promoter system for production of proteins and includes preferably the light inducible Rubisco promoter highly active in cotyledons. We have characterized a number of highly expressing Rubisco promoters by screening Rubisco cDNAs expressed in *Brassica campestris* cotyledons especially in non-illuminated conditions.

In addition to Rubisco promoter, other promoters can be used with this invention. Many proteinases and lipases are expressed specifically in the cotyledon of the germinating seeds. One of the most well-characterized is *Vigna mungo* sulfhydryl-endopeptidase (SH-EP), which is synthesized de novo in the cotyledons soon after the imbibition. Generally, the amount of SH-EP mRNA increases until the third or the forth day. The SH-EP promoter region (gene bank number: EMBL X51900) is fused with GUS gene to facilitate the measurement of the expression level during germination of the dicotyledonous seed.

In addition to promoters regulated in a tissue specific manner, inducible promoters, which can be activated by various stimuli, can be used. A class of genes known as heat shock or stress genes occurs in all organisms from bacteria to man. Transcription of these genes is initiated following a stress treatment (e.g., heat shock) and translation of the transcripts produces proteins that probably protect the cell temporarily. The production of heat shock mRNAs and proteins is only a temporary phenomenon and the expression of the heat shock genes levels off, after a few hours and then declines. If the temperature is increased slowly, rather than in a single step, an organism can withstand temperatures, which would otherwise be lethal, i.e., the organism can adapt to higher temperatures. Germinated seeds can be heated to increase heat shock promoter activity. Soybean heat shock (HS) mRNA levels have been shown to increase from a barely detectable level up to 15 000-20 000 copies after two hours of treatment at 40° C. The HS promoter region described in U.S. Pat. No. 5,447,858 can also be used in the expression system of the present invention as an inducible promoter. The HS promoter cloned by PCR is fused with GUS gene to measure the expression level during germination of the seed.

Any commercially interesting gene product may be produced by the present invention. These gene products include enzymes, which are heterologous to the plant. In other words, they are not native to the plant species, in which they are produced. Also included are enzymes, homologous to the plants, in which they are produced. Said homologous proteins are generally overexpressed using recombinant DNA techniques. Enzymes of interest include but are not limited to hydrolases, such as proteases, beta-glucanases, cellulases, hemi-cellulases, phosphatases, lipases, phospholipases, pectinases, amylases, amyloglycosidases, lysozymes, pullulanases and chitinases, peroxidases as well as lyases such as pectinolyase and isomerases, such as glucose isomerase.

It is also possible to produce structural proteins with the process and production system of the present invention. Some interesting embodiments of the present invention are for example collagen, gelatin, spidroin, silk protein, but also many other kinds of proteinaceous gene products can be produced, including enzyme inhibitors, such as the trypsin inhibitor, therapeutic peptides like interferons, insulin, neuropeptides, enkefalin, somatostatin, etc. Also other polyamino acids, such as polylysine and polyglutamate can be produced, as well as fibers, membranes, coatings, therapeutics or drugs, anti-scalants or food/feed additives and vaccines, such as LTB and growth factors, such as GM-CSF. Non-proteinaceous gene products can also be synthesized, including poly-beta-hydroxy-butyrate.

A great environmental advantage of the present invention is that the foreign gene is expressed mainly during germination and the germination can be carried out in confined conditions, whereby the gene product will not accumulate in the nature.

As the de novo synthesis during germination is a rapidly passing transient situation, the germination must be broken or interrupted before the desired gene product starts to decline. This can be achieved by recovering the desired gene product before its concentration declines by stopping the germination either by heating, codin-N2 (kilning) or alternatively, by crushing or excision of the germinated dicotyledonous seeds including the seedlings. If the germination is stopped by heating the desired gene product can be recovered as a crude dried product, with a good storability, which means that the enzyme can be retrieved in a crude storage stable form as well. The synthesis of the desired protein can also be stopped at its peak by crushing or excision of the germinating seed. If the germination is stopped by excision or crushing the gene product can be recovered as a crude mixture, it can be used as such or it can be down-stream processed, i.e. formulated, stored, and transported and stored. Preferably, it is used as such in e.g. in biotransformation processes. Naturally, the desired gene products can be isolated and purified by conventional well-known methods.

If the gene product is used for biotransformation, it is placed in contact with a substrate, i.e. a certain compound or a mixture of compounds, i.e. the gene product(s), often enzyme(s) are allowed to react with the compounds in the substrate. Either the gene product, e.g. the enzyme acts as an catalyze and modifies the compound(s) in the substrate, or alternatively the substrate or reagent contains at least one substance or compound capable of modifying the gene product, for example its folding patterns can be modified, glycosylation or deglycosylation can be carried out or it can be provided with substituent to facilitate conjugation of the gene product with other products.

In the present invention, after the germination, in conditions where a desired gene product can be produced, the substrate is enriched with the gene product. Seed derived composition include cotyledons, hypocotyls, root and in hypogeal type plants also epicotyl and sometimes small primary leaves. The gene product can be extracted or left in the composition.

The gene product may be a protein encoded by a gene provided by the expression system of the present invention or some other biochemical compound produced by a transgenic enzyme when the native gene products stored in the seed are mobilized by germination and used as such and allowed to act on an exogenously added substrate to provide the desired (bio)transformation of the substrate.

If the gene product is extracted from the composition, it can be used either in fresh or dried form. Drying can be performed in a heated dryer at 40-80° C. or in a lyophilizator at −20-−80° C. The dried material can be crushed or powdered. Before extraction, the composition may be mechanically disrupted and/or enzymatically treated bringing the total protein into a slurry or solution. The cellular debris may then be separated by any convenient means, such as centrifugation, sedimentation and/or filtration.

The supernatant or filtrate will normally comprise 1-40% (w/w) desired gene product of the total protein in the medium, preferably at least about 30% (w/w). When the desired product is not water soluble, it can for example be extracted with a convenient solvent. Alternatively, another process, which allows renaturation or solubilization and/or extraction of the product without loss of the activity of the desired product may be used.

After isolation of the protein of interest from the aqueous medium, the gene product can be purified in conventional ways. Since the gene product will comprise a substantial portion of the total protein present in the mixture, often being the greatest percentage of any individual protein, purification is greatly simplified. Furthermore, contaminants in the product after purification are not likely to be of physiological concern for any of applications of the gene products, including therapeutic applications.

If the gene product is not extracted from the composition but left in it, it can also be recovered in fresh form or dried form. The drying can be performed as described above. The dried material can further be crushed or powdered. The fresh material can be mashed by mechanical disruption or enzymatic treatment. Dried and fresh material can be used as a source of gene product. If the gene product is an enzyme, appropriate substrates can be added into the aqueous mixture or to the dried composition or used as fresh material.

In one embodiment of the present invention, the germinated dicotyledonous seeds, cotyledons and/or seedlings comprising one or more proteins of interest, can be used as a supplement in feed products. The germinated dicotyledonous seeds can be mixed with normal non-transgenic seeds to obtain the desired concentration of the gene product of interest in an animal feed product.

Germinated seed derived mixtures or compositions can be dried and stored. The gene products can be isolated or left in the material, when for example the recombinant protein is useful in feed applications. The gene products can be used to increase protein value of animal feed or it can be for example a growth hormone or a vaccine. In addition, labile or toxic substances can be produced in a strictly controlled manner, which combines efficient protein production with ecological aspects and agricultural interests.

The invention is described in more detail below. The examples and experimental details are disclosed to provide an improved understanding and guidance for those skilled in the art.

Example 1

GUS Gene Expression in Germinating *Brasssica campestris* Seeds

GUS expression is demonstrated with a histochemical assay. We used four different promoters to regulate the GUS expression. The promoters used are Soybean heat shock promoter, *Vigna mungo* endopeptidase promoter, *Nicotiana tabacum* pr-promoter and CaMV 35S promoter. Promoter sequences were produced by PCR with plant total DNA as a template.

Figure 3:
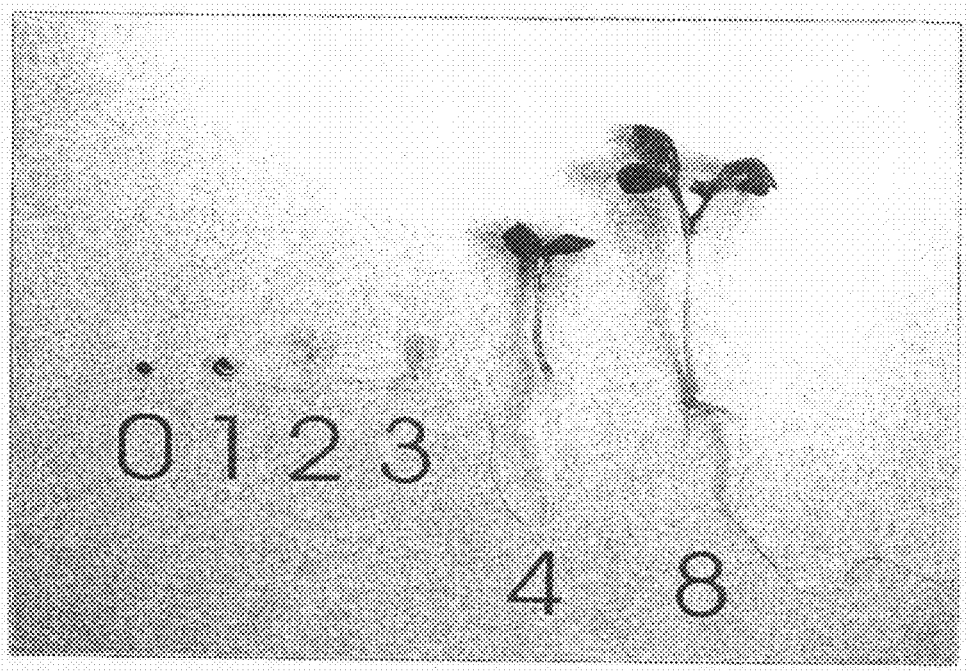
FIG. 3 depicts various germination stages of a *Brassica campestris* seed, indicated as days after the onset of germination.

The promoters were linked to the GUS gene using NcoI enzyme. The promoter-GUS constructs were cloned in a plant transformation vector, pGPTV-hpt (Becker et al. 1992. Plant Mol. Biol. 20:1195-97). *B. campestris* was transformed according to the protocol described by Kuvshinov, V. et al. (Plant Cell Reports 18:773-777, 1999). The transgenic plants were grown in greenhouse until they produced seeds. The transgenic seeds were germinated and used for the histochemical GUS assay. The results are shown in FIGS. 1-3.

On the left side in FIG. 1A a germinated seed of a transgenic *B. campestris* expressing the GUS gene is shown. The GUS gene is linked to the soybean heat shock promoter. On the right side, an untransformed control seedling is shown.

In FIG. 1B germinated seed of transgenic *Brassica campestris* expressing the GUS gene is shown. The GUS gene is linked to the endopeptidase promoter.

In FIG. 1C the germinated seed of transgenic *Brassica campestris* expressing the GUS gene is shown. The GUS gene is linked to the salicylate inducible promoter.

In FIG. 1D the germinated seed of transgenic *Brassica campestris* expressing the GUS gene is shown. The GUS gene is linked to the 35S promoter.

FIG. 2 shows the colorless buffer solution containing the substrate β-Glucuronide (100 µg/ml) which by the action of the GUS enzyme produced by a germinated transgenic seed is enzymatically converted into the blue-colored glucopyranosiduronic acid and aglycone.

FIG. 3 shows various germination stages of a *Brassica campestris* seed, indicated as days after the onset of germination. The surface sterilized seeds were germinated under in vitro conditions, illuminated for 16 hours at the temperature of 22° C., and under non-illuminated (dark) conditions for 8 hours at the temperature of 18° C.

Example 2

Storage Proteins are Converted to Rubisco Proteins in Developing Sprouts

Figure 5:
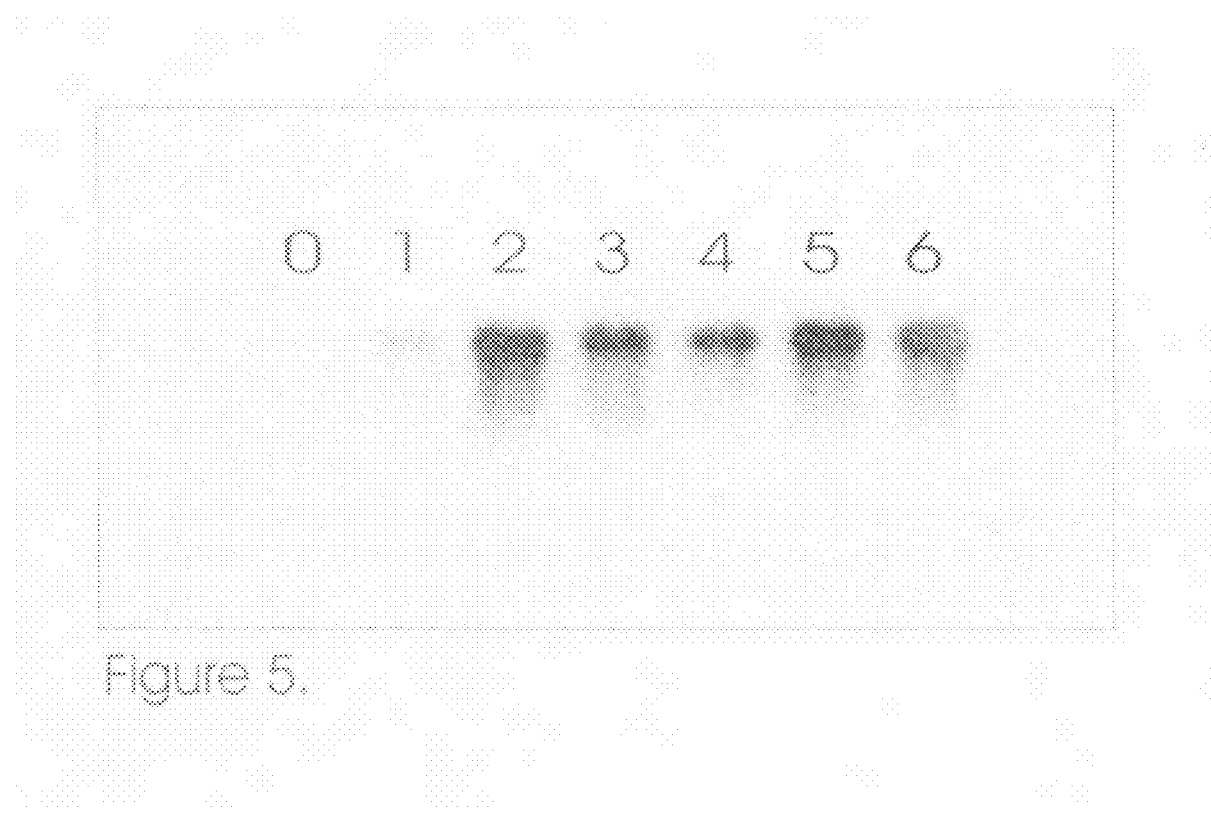
FIG. 5 shows a northern blot of germinated seeds using RNA probes. The samples were collected daily, starting from dry seed.
Figure 6:
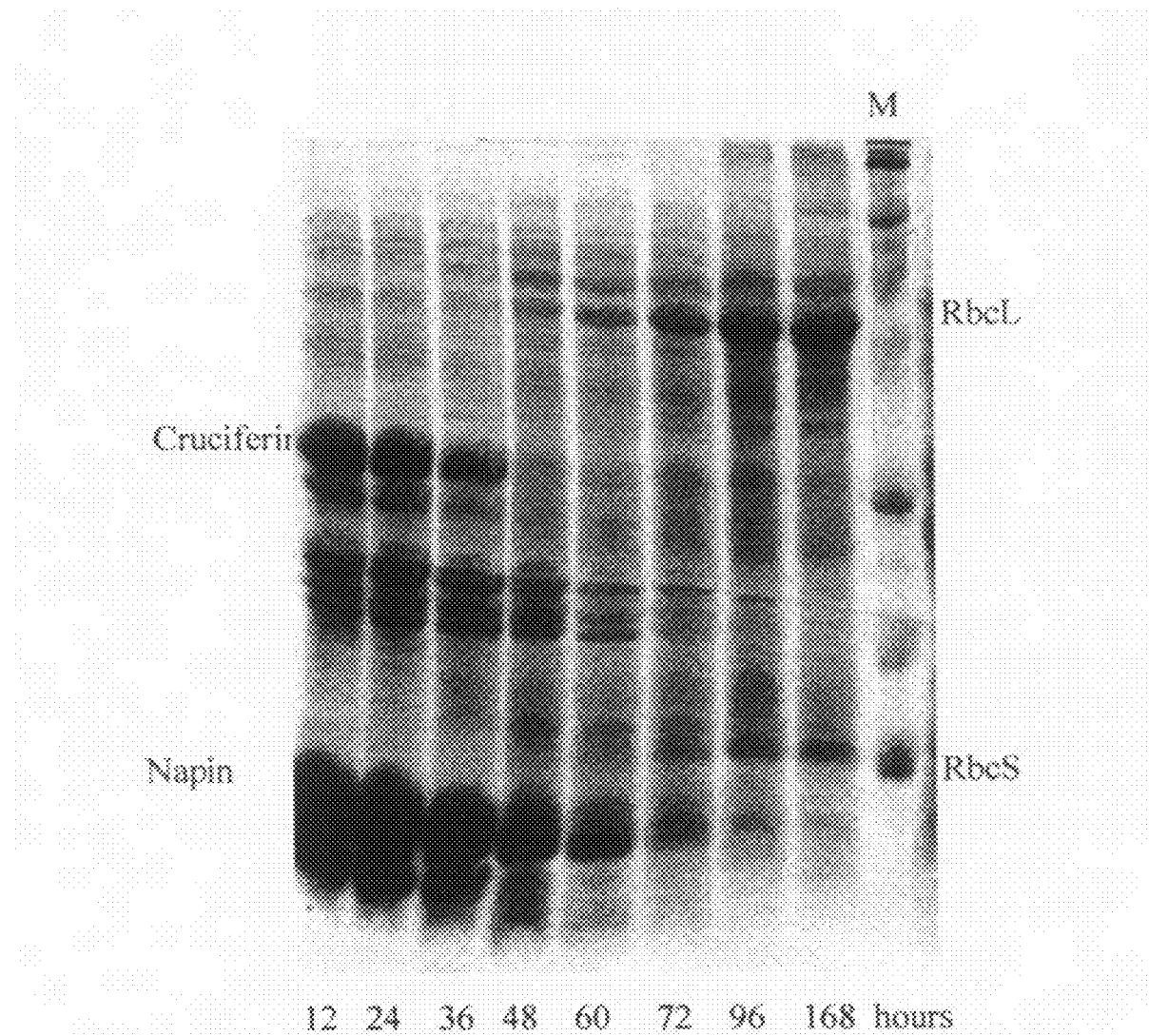
FIG. 6 shows an SDS-PAGE gel of total soluble proteins of germinating seeds of *Brassica campestris*. Seeds were germinated in an airlift tank for 12-168 hours and a sample for total soluble proteins was harvested at time points shown below the figure.
Figure 10:
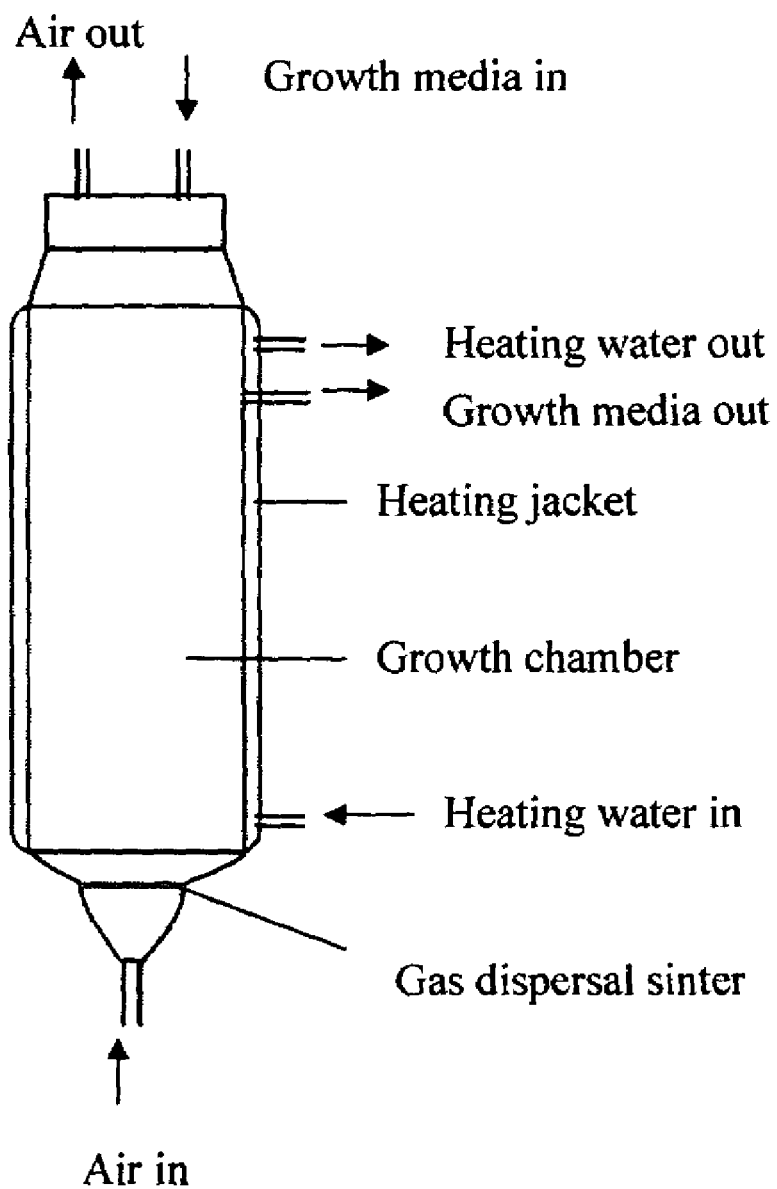
FIG. 10 is a schematic illustration of laboratory scale 10-L spouting equipment.

*Brassica campestris* seeds were germinated for 12-168 hours in an airlift tank (shown in FIG. 10). The total proteins were extracted and separated by 15% SDS-PAGE. The gel was stained with Coomassie blue. Between 36 and 60 hours, the degradation of storage proteins and de novo synthesis of Rubisco was clearly visible. This result is illustrated in FIG. 6. Similarly, FIG. 5 illustrates germination experiment with *Brassica rapa* (*campestris*) seeds. The amount of Rubisco proteins is clearly increased after the third day.

Figures 7A, 7B:
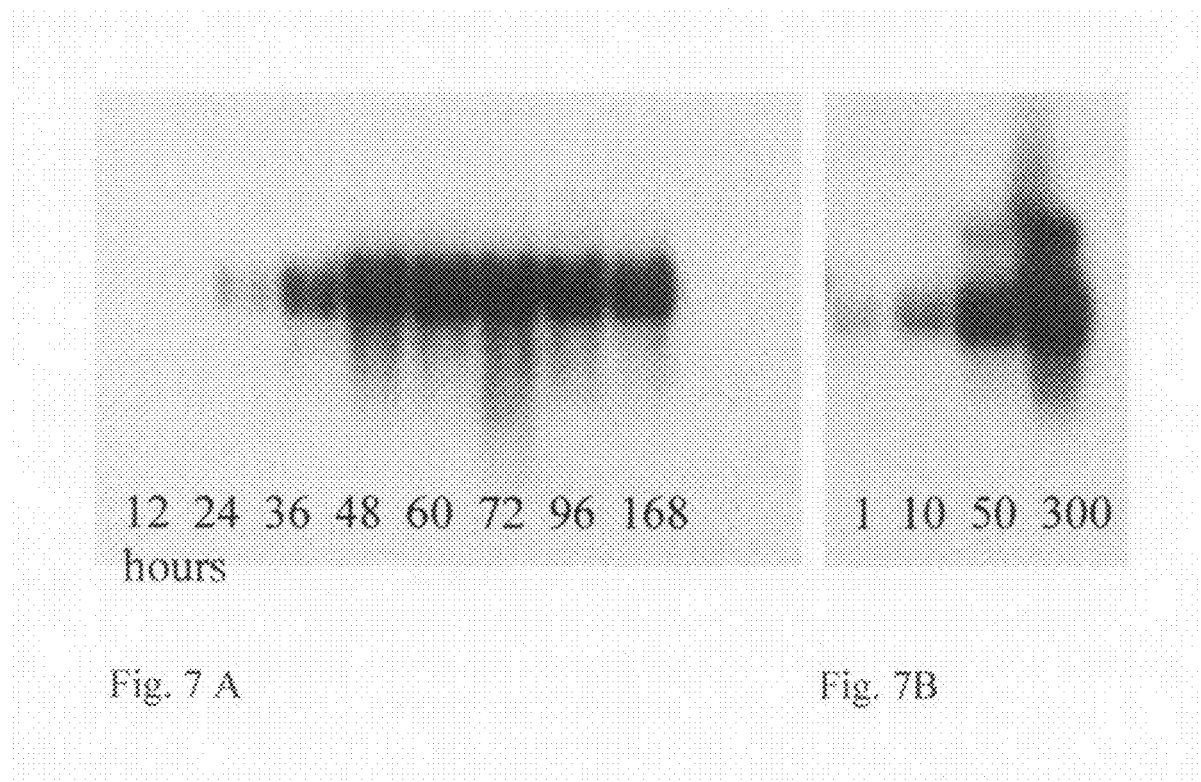
FIG. 7A shows Northern blot showing the synthesis of Rubisco SSU mRNA after 24-36 h of sprouting in an airlift tank. Total RNA was isolated form spouts germinated from 12 to 168 hours. Duration of sprouting is shown below the blot.
FIG. 7B shows unlabelled Rubisco RNA produced by in vitro transcription was loaded as a control on the same filter. Amount of the control RNA is shown in picograms below the blot.

FIG. 7A illustrates Northern blots showing synthesis of Rubisco SSU mRNA after 24-26 hours of sprouting in an airlift tank. Total RNA was isolated from spouts germinated form 12-168 hours. FIG. 7B shows unlabelled Rubisco RNA produced by in vitro transcription as loaded as a control.

Figure 4:
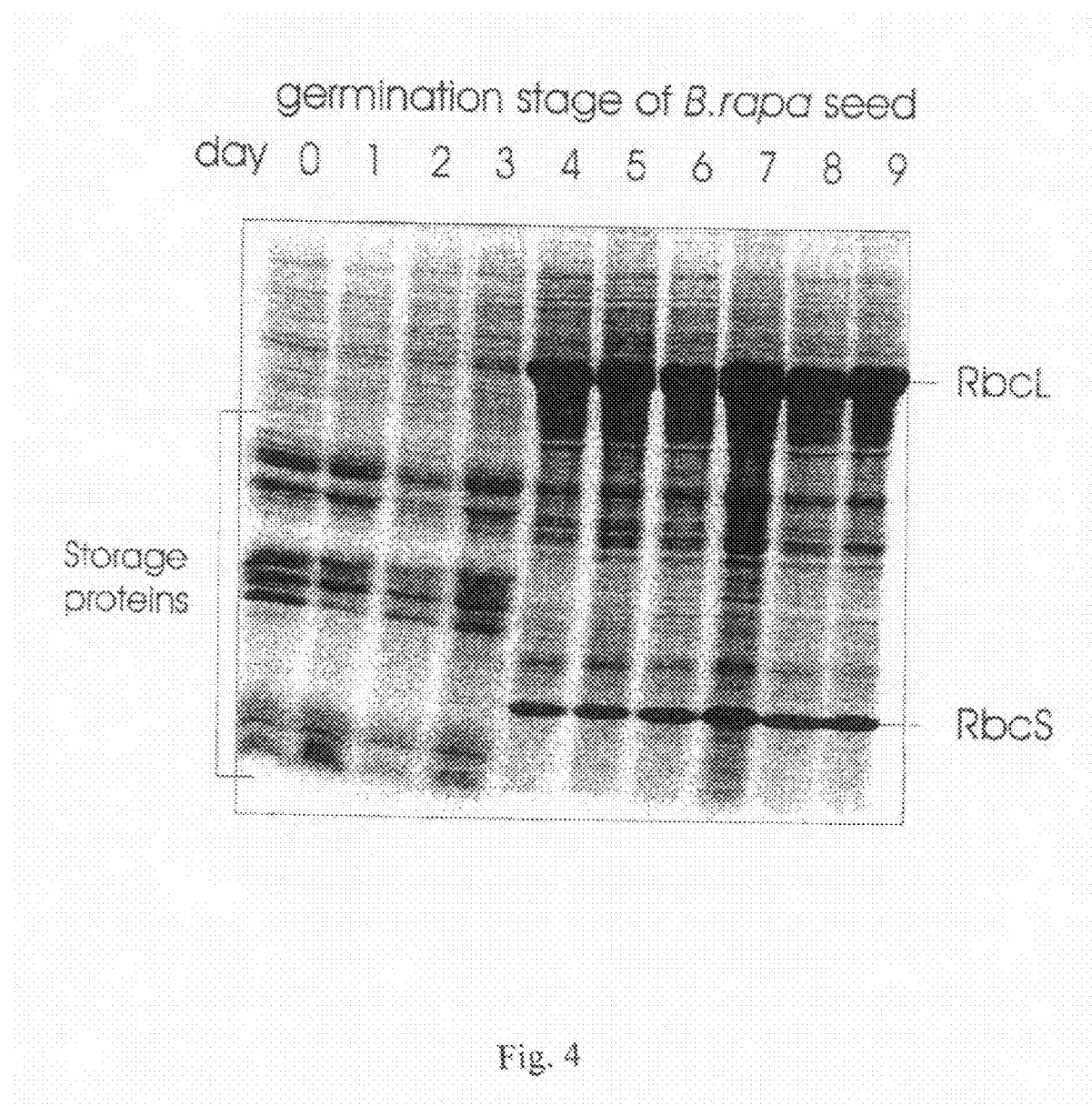
FIG. 4 shows a SDS-PAGE gel of germinated seeds of *Brassica campestris* (*rapa*). The samples were collected daily, starting from the dry seed. The storage proteins and Rubisco subunits are marked in the Coomassie-stained gel. After three days of germination, the degradation of storage proteins and de novo synthesis of Rubisco proteins is clearly visible.

FIG. 4 shows a SDS-PAGE gel of germinated *Brassica campestris* seeds. The samples were collected daily, starting from the dry seed. Material was homogenized in liquid nitrogen and resuspended in 50 mM Tris, pH 8.0, in the presence of 850 mM NaCl. After centrifugation, the clear supernatant was mixed with a loading buffer. The storage proteins and Rubisco subunits are marked in the Coomassie-stained gel. After three days of germination, the amount of Rubisco protein produced per day is significant, showing de novo synthesis of Rubisco protein from the storage proteins.

FIG. 5 shows a northern blot of germinated *Brassica campestris* seeds using RNA probes. The samples were collected daily, starting from dry seed. The antisense sequence probe contains 197 bp from exon 3 and 153 bp from the 3'-UTR region of Rubisco small subunit cDNA (unpublished). The probe is generated from pBluescript plasmid by the T7-promoter using DIG-UTP in the reaction. Each lane was loaded with 3 µg of total RNA. RNA was extracted using the Qiagen RNeasy Plant Mini Kit. Hybridization was made with DIG Easy Hyb buffer essentially according to the manufacturer's protocol.

Example 3

The Preparation of Novel rbcS-Promoters for the Expression System

Based on the strong Rubisco protein synthesis in germinating seeds it seems that Rubico promoter is a very strong promoter in rapeseed sprouts. Therefore, we decided to characterize Rubisco promoters in the germinating seeds and characterize the promoters further.

A cDNA library was constructed in order to identify the most abundant types of Rubisco mRNA to be expressed in cotyledons of germinating *Brassica rapa* (*campestris*) seeds.

Total RNA was isolated from four days old *Brassica* seedlings, and a mRNA fraction was isolated from the total RNA preparations using oligo(d)T cellulose. A first strand cDNA was synthesized using oligo(d)T with M-MLV (Point mutant) reverse transcriptase. The next PCR step was carried out with a forward primer e3a 5'-CAUCAUCAUCAUCAACCGT-CAAGTCCAGTGCATCAGTTTCAT-3' (SEQ ID NO: 4) specific to the 3$^{rd}$ exon of Rubisco SSU coding region and the reverse primer atu 5'-CUACUACUACU-ATTTTTTTTTTTTTTT-3' (SEQ ID NO: 5), an oligo(d)T derivative, specially designed according to CloneAmp procedure (Life Technologies). Both primers comprised on their 5'-terminal end several dUMP residues, which were destroyed by the enzyme UDG (Uracil DNA Glycosylase). The PCR step was carried out in 2 cycles, and subsequently the PCR product was digested by UDG and directly inserted into the linearized pAMP1 vector (Life Technologies) containing special protruding 3'-terminal ends compatible with protruding 3'-terminal ends of the RT-PCR products. The insert containing vector was transformed into competent *E. coli* strain XL-1. One hundred plaques were selected and analyzed. Inserts from plasmid DNA were amplified by PCR and the resulting PCR-products were sequenced. Relative number of separate colonies containing inserts of each type was calculated by the aid of sequence analysis.

Sequence analysis of the cloned 3'UTRs showed striking quantitative differences between different Rubisco mRNA species. The sequence named '56' comprised 56% of all the Rubisco mRNA cloned. The other sequence named '29' comprised 29% of all the Rubisco mRNA. The rest 15% of the clones corresponded to the other types of Rubisco mRNAs.

The 29-type and 56-type sequences received from the cDNA library were compared to published sequences. The sequence alignments indicated that these Rubisco mRNAs are expressed from novel Rubisco promoters. The 29-type sequences are called rbcS-2 and the 56-type sequences are called as rbcS-4, respectively.

Cloning Rubisco Promoters Obtained from *Brassica campestris*

Based on the '56' and '29' type of sequences reverse primers were designed to be used in subsequent steps of promoter cloning.

Cloning of rbcs-2 Promoter

An EST-library was constructed first. The most common UTR found was UTR2, which was used to design reverse primers for Genome Walking step. Genomic DNA of *Brassica rapa* was digested by EcoRV, DraI, HincII, PvuII, SmaI and SspI and ligated to adapters (5'-GTAATACGACTCAC-TATAGGGCACGCGTGGTCGACGGCCCGGGCTGGT (SEQ ID NO: 6) and 5'-p-ACCAGCCC-NH$_2$-3'(SEQ ID NO: 7) to get six DNA libraries.

The next PCR amplifications (first and nested) were performed with adapter primer AP1 5'-GTAATACGACTCAC-TATAGGGC-3' (SEQ ID NO: 8) and UTR2-specific L1 primer 5'-GGCCACACTTGACAATCCGATATAACAT-GCCTCA-3' (SEQ ID NO: 9).

Nested PCR was conducted with AP2 primer 5'-ACTAT-AGGGCACGCGTGGT-3' (SEQ ID NO: 10) and nested UTR2-specific L2 primer 5'-CAAATGGAAATGAAAT-GAGGTAG-3' (SEQ ID NO: 11).

The longest 900 bp product was obtained by using a DraI DNA library. This fragment was cloned into a pGEM3Zf(+) vector and sequenced. The sequence was compared with the sequences in GenBank database. The most homologous sequence found was *B. napus* rbcS (accession number X61097).

Near the 5'-end of one of the clones received (Rud3) was a 22 nt long stretch lacking from *B. napus* rbcS (beginning from 1037 nt of *B. napus* rbcS). Two reverse primers, RbNco and RbSiB, downstream from the putative transcription initiation site (based on the homology with X61097) and two forward primers, BNRb1 and BNRb3, based on X61097 homology, were designed. Full-length rbcS-2-gene was amplified using BNRb1 as a forward primer and UTR2-L2 as a reverse primer. Subsequently, two promoters of different length were amplified in nested PCRs using combinations of BNRb3 as a forward primer and RbSiB (with signal peptide) as a reverse primer, or BNRb3 as a forward primer and RbNco as a reverse primer (without signal peptide).

Cloning of rbcS-4 Promoter

Promoter cloning was conducted in several steps. Two reverse primers (for the first and nested PCRs) matching with the same sequences on the beginning of the first exons of three published Rubisco genes were used for the first step of Genome Walking.

Genomic DNA was isolated from *Brassica rapa* leaves and divided into six fractions. Each fraction was digested by one of six restricting enzymes (EcoRV, DraI, PvuII, StuI, SspI, XmnI) and ligated with Genome Walking adapters (Clontech) mentioned above. Each restriction-ligation mixture represents a genomic DNA library.

The next step included two successive PCRs (first and nested) using adapter-specific AP1 and AP2 (forward) and gene-specific (reverse) primers. The PCR was started by using three different reverse primers, annealed to different parts of the first exon of Rubisco SSU gene in order to get the overlapping PCR products listed below.

```
(RbcS-RN:
                                      (SEQ ID NO: 12)
5'-ACCCGGGCCCAGGAGAGCATAGAGGAAGCC-3',

RbcS-R1:
                                      (SEQ ID NO: 13)
5'-CGGTGAATGGAGCGACCATCGTGGCTTGAG-3',

RbcS-R2:
                                      (SEQ ID NO: 14)
5'-CTGTGAATGGAGCAACCATGGCCGCTTGAG-3'.
```

The six genomic DNA libraries described above produced amplification products after nested PCR. These products were directly cloned into pGEM-T-Easy vector (Promega) by TA-cloning. Colonies were screened by PCR using M13-universal and reverse primers. Colonies carrying plasmid DNA with insert were grown in liquid cultures and plasmid DNA isolated was used for sequencing analysis.

A total number of about ninety plasmid DNA insert-containing clones were analyzed. Based on data obtained from the sequencing analysis the sequences were divided into five groups according to sequence similarities. Three promoters were identified to be similar to the ones published in GenBank. Moreover, PCR using specially designed forward primers, specific to the cloned promoter regions, and reverse primers, specific for the '56'-type of 3'UTR (rbcS-4 type of 3'UTR) allowed identification of putative promoters having the 56 type of 3'UTR (rbcS-4 type of 3'UTR) in the genome. This promoter was called '56A'.

Based on the obtained sequences new reverse primers were designed to make next PCR step with the same forward primers (AP1, AP2) and the new reverse primers and using the same genomic DNA libraries. This procedure was repeated four times. The resulting sequences obtained after the fourth PCR cycle allowed us to design promoter-specific forward primers. The reverse primer was designed to include a special site for BpiI to create an NcoI-compatible restriction site. PCR using these primers and HiFi KOD polymerase enabled identification of the '56' type of promoter rbc-4A (SEQ ID NO: 1) among other sequences. By means of GenomeWalking techniques another promoter with the '56' type 3'UTR was found bound in the genome. This rbcS-4B promoter (SEQ ID NO: 2) was 98% similar to rbcS-4A on the length of about 230 nt region in (1953-2175 nt SEQ ID NO: 1 and 794-1016 nt in SEQ ID NO: 2), but distal parts of rbcS-4A and rbcS-4B showed less than 40% similarity. FIG. 2B gives an alignment of −267 to +33 nt regions of these two promoters. RbcS-4B promoter was also cloned with proof-reading KOD polymerase and its functional activity was studied further.

By using the same approach, totally four steps of Genome Walking were applied to clone the rbcS-4A promoter and two steps were applied to clone rbcS-1, rbcS-3 and rbcS-5 promoters (SEQ ID NO: 21, SEQ ID NO: 22 and SEQ ID NO: 23, respectively). After the final step of Genome Walking whole length promoters were cloned using the proof-reading Pfu DNA polymerase enzyme. The 3'-terminal ends of the cloned promoter sequences were designed so that they can be ligated with reporter genes. GenBank BLAST system was used to analyze the promoter sequences obtained. *Brassica* promoters having accession numbers X55937 and X75334 showed similarity of up to 98-99% with rbcS-3 and rbcS-5 promoters, respectively.

The Genome Walking data showed that there were two partially different rbcS-4 (called rbcS-4A and rbcS-4B) promoters connected to the same 3'UTRs and being very similar on the last 230 bp on their 3'-terminal ends (rbcS-4A is SEQ ID NO: 1; rbcS-4B is SEQ ID NO: 2). On the other hand, the distal parts of the promoters show the same low level of homology (40%) as they show in alignment with other Rubisco promoters.

Example 4

Fusion-Constructs rbcS-4A-GUS, rbcS-4A-HSA, rbcS-4B-GUS, rbcS-2-GUS, rbcS-2-HSA, rbcS-2-Ab(L+H)-1C2, rbcS-4A-Ab(L+H)-1C2, rbcS-2, TNFR-Fc and rbcS-4-TNFR-Fc The promoters were amplified with reverse primers to get NcoI-compatible restriction site on their 3'-terminal ends. Vector pCAMBIA1301 (CAMBIA) containing GUS gene with NcoI site on its 5'-terminal end was used. HSA fusion constructs were designed in a pBIN19-based plasmid pGPTV with an inserted HSA gene (SEQ ID NO: 15). RbcS-4A and rbcS4B were cut out by BpiI, HindIII. RbcS-2 was cut out by NcoI, HindIII. RbcS-4A, rbcS-4B, and rbcS-2 were cloned into pCAMBIA1301 or pGPTV vectors opened by NcoI, HindIII. The terminators used for these constructs were as follows: nos-terminator in GUS-containing pCAMBIA1301 vector, and rbcS-4 type of 3'UTR plus part of known *Brassica campestris (rapa)* rbcS terminator from GenBank was used in HSA-containing pGPTV plasmids.

Constructs Rbcs-2-Ab(L+H)-1C2 and RbcS-4-Ab(L+H)-1C2 contain the same antibody regions and the same terminator (polyA) signal from the natural *Brassica* rubisco RbcS-4 gene (directly from the genome). The antibody protein molecule was originally developed against hevein 1C2 antigen. RbcS-2-Ab(L+H)-1C2 consists of RbcS-2 promoter, light chain (anti-hevein 1C2) (SEQ ID NO: 16) coding region, rbcS-4 terminator (SEQ ID NO: 17), another RbcS-2 promoter, heavy chain (anti hevein 1C2) (SEQ ID NO: 18) coding region, and another Rbcs-4 terminator. The RbcS-4-Ab(L+H)-1C2 construct consists of Rbcs-4 promoter, light chain (anti-hevein 1C2) (SEQ ID NO: 16) coding region, RbcS-4 terminator, another RbcS-4 promoter, heavy chain (anti-hevein 1C2) coding region (SEQ ID NO: 18), and another RbcS-4 terminator.

For the constructs Rbcs-2-Ab(L+H)-1C2 and RbcS-4-Ab(L+H)-1C2, the rbcS-2 and rbcS-4 promoters were cut by SalI, HindIII and ligated with pVK1-CHC(constant heavy chain)-rbcS-4-terminator, digested with SalI, and HindIII providing the pVK1-RbcS-2(Rbcs-4A)-promoter-CHC-RbcS-4-terminator. RbcS-4 terminator was originally cloned with CHC by BsiWI, EcoRI. Variable heavy chain region of 1C2 antibody (VH-1C2) was cut out by BpiI, Bsp120I and cloned into a pVK1-Rbcs-2(Rbcs-4)-promoter-CHC-RbcS-4-terminator vector by the same sites. The resulting plasmid was the plasmid containing whole H (heavy) chain unit. The same strategy was used to get the whole L (light) chain unit. L chain unit was then cloned into pCAMBIA1301 vector from where the 35S-GUS region was removed. This was pCAMBIA1301-L-chain. In the final step the H-chain unit was inserted into pCAMBIA1301-L-chain vector to get the final pCAMBIA1301-H-L. The plasmid was used for plant transformation using *Agrobacterium*-mediated strategy.

Ig-TNFR (ENBREL) construct contains rbcS-2 or rbcS-4 promoters, TNFR (tumor necrosis factor receptor) part (489 nt) (SEQ ID NO: 19) comprising the IgCHC part (CH2 and CH3 domains) and terminators. TNFR part was cloned directly from human mRNA by reverse transcription followed by PCR, ligated into pGEM-T-Easy plasmid by TA-cloning procedure and sequenced from both directions with M13-universal and reverse primers. Ig CHC part was obtained by PCR and sequenced thereafter. Cloning strategy included ligation of Ig CHC part by BsiWI site and introducing promoter into pVK1 plasmid (pUC19 derivative), containing rbcS-4-terminator. Then TNFR part digested by BsmB1 was introduced into this plasmid, and whole the insert was re-cloned into big pCAMBIA1300 or pCAMBIA2300 plasmids.

IgCHC part was obtained in two variants. The first was without any changes in its 3'end and the second one contained KDEL signal in its 3'end. This signal is 12 nt long sequence AAAGACGAGCTG (SEQ ID NO: 24) and is introduced just before the STOP-codon. Several terminators were used in the Ig-TNFR constructs. One was rbcS-4 terminator (about 500 nt) being the same as used in antibody constructs. Another terminator was a longer version of the rbcS 4-terminator (being about 2 kb). Still another terminator used was from *Arabidopsisis* VSP1 (vegetative storage protein-1 gene), the part situating right behind the STOP codon and before cleavage site was used and was connected with part of rbcS-4 terminator (SEQ ID NO: 20). In some of the constructs one or two MAR (matrix attachment regions) sequences (about 2 kb) were also introduced. In case the construct contained two MAR sequences they were introduced before the promoter and after the terminator.

Example 5

Plant Transformation

To exemplify the functionality of the novel promoters according to this disclosure, we transformed plants of *Brassica* species, *Nicotiana tabacum* plants and *Camelina sativa* plants. One skilled in the art is able to transform plants of other species.

*Brassica* plants were transformed with *A. tumefaciens* strain LBA4404 carrying the pCAMBIA1301 or pGPTV-HPT binary vectors by leaf disk inoculation. Tobacco plants *Nicotiana tabacum* cv. Samsung were transformed with *A. tumefaciens* strain LBA4404 carrying pGPTV-HPT binary vectors by leaf disc inoculation. Putative transformants were selected on 30 mg/l hygromycin. Positive lines were transferred to the greenhouse for further studies

*Camelina* plants were transformed with *A. tumefaciens* strain C58 (helper plasmid pGV3850) carrying the pCAMBIA1300 binary vectors by leaf disc inoculation. Putative transformants were selected on 20 mg/l hygromycin. Positive lines were transferred to the greenhouse for further studies.

The sequences and percentage of the distribution of different types of sequences in germinating seedlings is presented in Table 2.

TABLE 2

The sequences and percentage of distribution of different types of mRNA.

| SEQUENCE | Germinating seedling |
|---|---|
| Type I | 29% |
| Type II | 15% |
| Type III | 56% |

Example 5

Comparison of Different Constitutive and Inducible Promoters for the Overexpression of Transgene (GUS) in Tobacco and *Brassica campestris* Seedlings Tobacco and *Brassica*-plants were transformed with constructs containing various promoters linked to GUS-gene. The plants were grown in greenhouse and the seeds were collected and germinated. Germinating seedlings were frozen with liquid nitrogen and grinded. Proteins were extracted with phosphate-EDTA buffer. Samples were centrifuged and supernatants were analyzed using β-glucuronidase activity detection kit (Sigma). Protein concentration of samples were analyzed with Protein assay reagent (Biorad) using BSA as a standard.

TABLE 3

The specific activities of GUS with different constitutive and inducible promoters in tobacco and *Brassica campestris* on day 7.

| PLANT | PROMOTER | SPECIFIC ACTIVITY (nmol MU/min/mg of soluble protein) |
|---|---|---|
| Tobacco | B. Rubisco type I | 7 |
| B. campestris | Heat shock | 44 |
| B. campestris | Heat shock amylase | 5 |
| B. campestris | 35S | 28 |

When following the promoter activity in germinating seed during germination in a series of seven days an exponential increase in specific activity for example in Rubisco promoter was detected. The specific activity of Rubisco promoter was 0.25 on the 4th day, 0.5 on the 5th day, 1.6 on the 6th 5 day and 7 on the 7th day.

Example 6

Analysis of Chloroplast Development Inhibitors for Rubisco Protein and mRNA Levels in Germinating Seeds To increase the yield of recombinant protein, we decided to down regulate the expression of endogenous genes. Because about 50% of the protein in the cotyledons is derived from the chloroplast genome, we focused on down regulation protein expression in chloroplasts. This does not interfere with transgene expression since transgenes are introduced into the nuclear genome.

Transcription and protein synthesis in the chloroplast can be inhibited by antibiotics, because chloroplast ribosomes are similar in structure to those of bacteria. Chloroplast ribosomes are 70S in size, comprising a large 50S subunit and a small 30S subunit. Chloroplast ribosomal proteins are encoded by both nuclear and chloroplast genes.

Chloroplast protein synthesis is controlled largely at the post-transcriptional. Level and can be repressed by the inclusion of antibiotics such as streptomycin in the sprouting medium. Streptomycin binds to the 16S rRNA and causes the ribosome to misread the mRNA sequence producing incorrect and non-functional protein.

Inhibition of endogenous Rubisco genes can be inhibited during sprouting, through use of streptomycin. Timing is critical to achieve strong inhibition. If streptomycin was added too early, sprout development was delayed. If streptomycin was added too late, the storage reserves were already used for endogenous protein expression and no increase in recombinant protein expression already used for endogenous protein expression and no increase in recombinant protein expression was detected.

Figure 8:
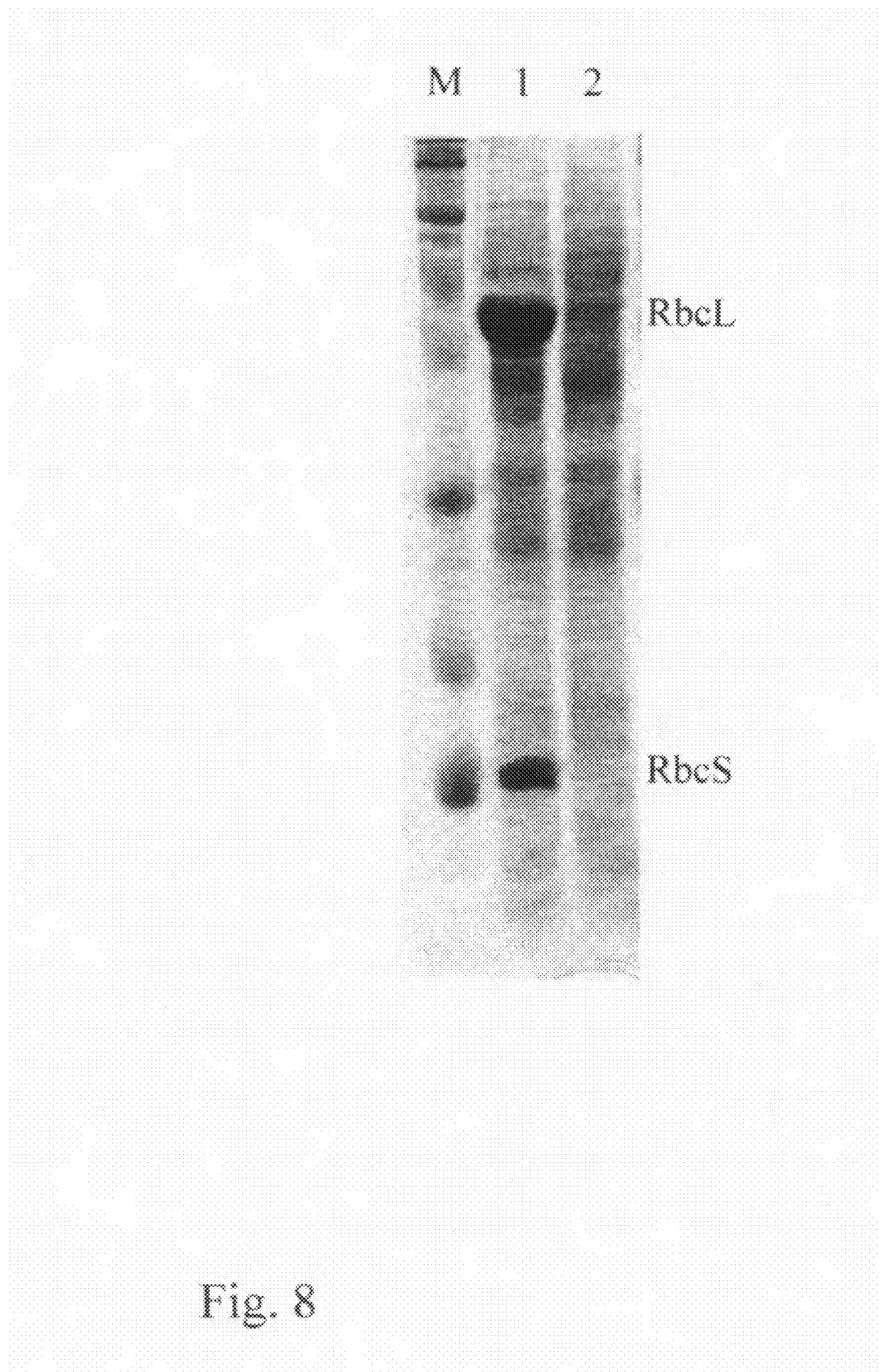
FIG. 8 shows an SDS-PAGE gel of total proteins of transgenic rapeseeds sprouted in an airlift with (lane 1) and without (lane 2) of streptomycin at 100 mg/L.
Figure 9:
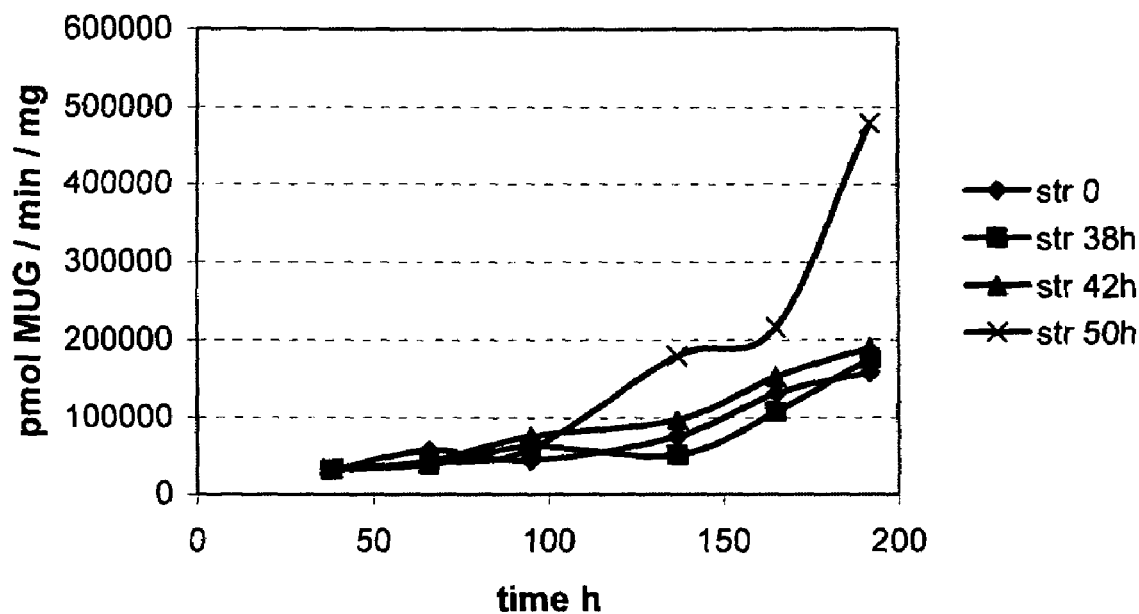
FIG. 9 illustrates gusA gene expression in transgenic rapeseeds. Transgenic rapeseeds expressing gusA reporter gene were germinated in an airlift tank with streptomycin added to the medium (100 mg/L). Steptomycin was added 0.38.42 or 50 hours after germination.

The best result wad obtained when 100 mg/l streptomycin was added 48 to 50 hours after the initiation of germination. With streptomycin treatment, 100-400% increases in recombinant protein extension were obtained. The accumulation of both Rubisco subunits were prevented and the specific activity of GUS increased 2.5 fold when streptomycin was used. Results are shown in FIGS. 8 and 9.

Example 7

Sprouting Equipment and Experiments to Modify Production

In an experimental set-up, the volume of a laboratory-scale sprouting vessel is 10 liters. FIG. 10 shows a schematic drawing of the vessel.

The vessel is made of two glass cylinders one within the other. The inner cylinder forms a growth chamber where seeds are sprouted in a medium consisting of tap water. Heated water is circulated through the space between the cylinders and this acts as a heating jacket. The temperature can be regulated accurately by using a thermally controlled water bath to heat the circulating water. The water in the growth chamber is aerated by pumping pressured air through a gas dispersal sinter at the bottom of the cylinder. Air can be sterilized by using a 0.2 μm filter. For efficient aeration, 15% of medium volume consists of small air bubbles. Air stirs the medium effetely and enhances the movement of the sprouts. The growth medium can be circulated optionally thought the growth chamber. Normally tow or four chamber volumes are circulated through the growth chamber per day.

In the 10-liter sprouting vessel, 400-800 g of seeds can be sprouted, depending on the cultivation time. In case of overload, sprouts stick together and are not uniformly lit. Light is needed to regulate sprout development and of the induction of the promoter driving the transgene of interest. However, sprouts do not need light as an energy source because about 48% of the dry weight of rapeseed is storage oil that is used for the initial growth of the sprout.

Microbial contamination, especially by salmonella species, is a risk when sprouts are produced commercially for human consumption. For recombinant protein products, seeds can be washed with water and surface-sterilized using hypochlorite solution. Sprout can even be surface-sterilized during sprouting, by the addition of mild hypochlorite solution directly into the growth medium. Eventually, the hypochlorite is diluted out with pure water or growth medium. In our experiment on plate count agar, the sprouts showed no bacterial growth after sterilization with 1% sodium hypochlorite.

Imbibition of dry seeds is initiated by placing them in the airlift tank filled with water. Later, nutrients and other substances can also be added. For example, $KNO_3$ cannot be added any earlier than 6 hours after the start of germination, or it will inhibit sprout growth.

Germination and subsequent sprouting is faster in an airlift tank than on agar plates or in soil. In an airlift tank, the sprout reaches the same developmental stage after 3 days as it does after 4 days cultivation on agar. The sprouting process is rapid: storage proteins are mobilized within 48 h and the Rubisco protein is synthesized within 96 hours. Recombinant protein expression occurs preferably between 48 and 96 h after most of the storage recourses have been used and the cotyledon begins to turn into a more leaf-like structure. The Rubisco promoters as described in Example 3 for recombinant protein expression are activated after 36 hours.

Figure 11:
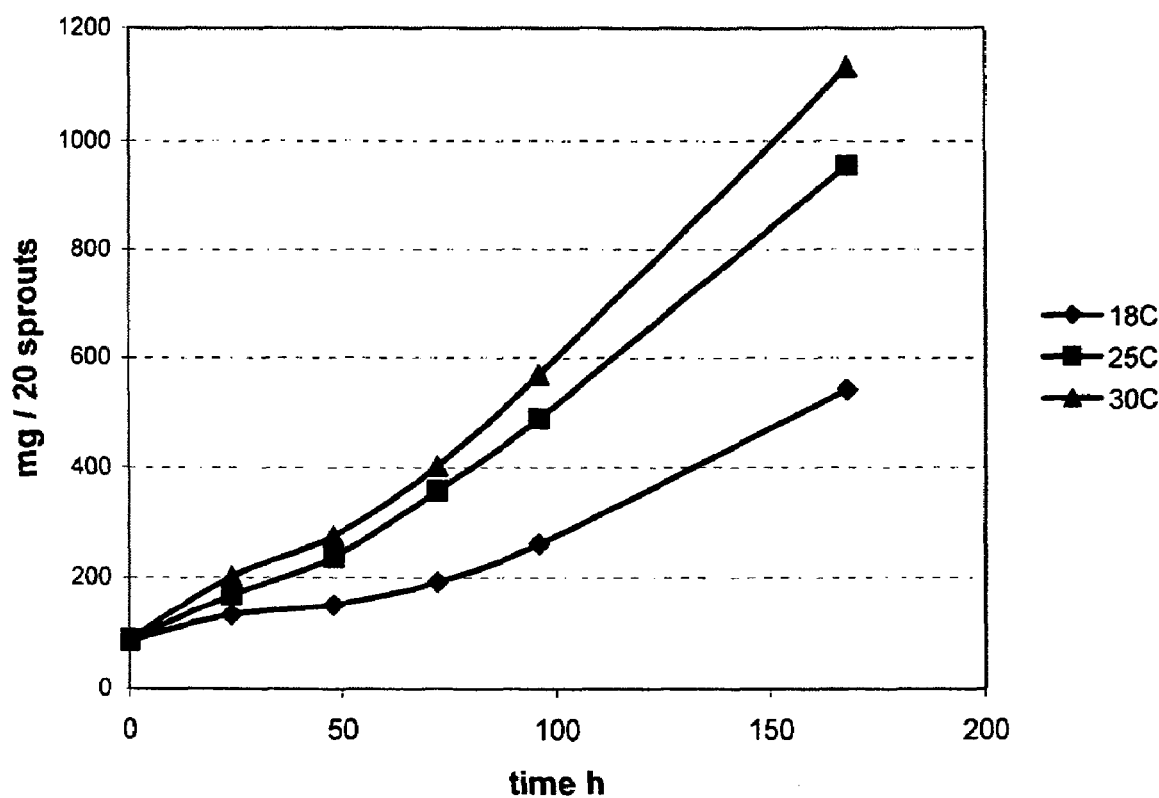
FIG. 11 shows results of sprouting of rapeseeds at various temperatures (18° C., 25° C. and 30° C.).
Figure 12:
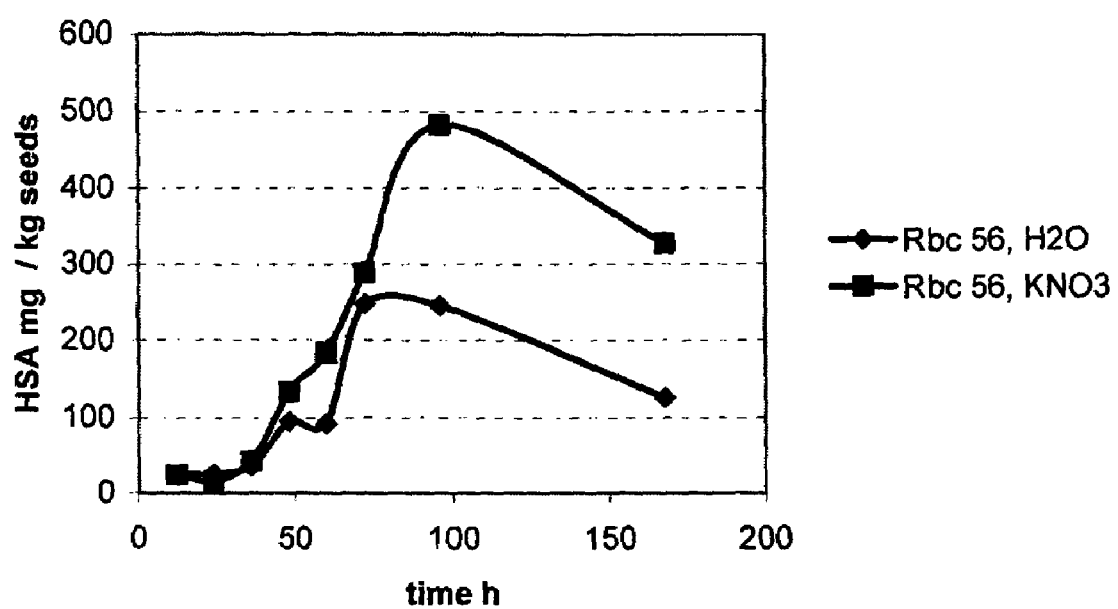
FIG. 12 illustrates the positive effect of nitrogen fertilizer (potassium nitrate) on the growth and productivity of transgenic sprouts. The growth rate is measured as an increase in fresh weight during sprouting.

Sprouting can be accelerated by increasing the growth temperature as is shown in FIG. 11 and by using appropriate nitrogen fertilizer, as is shown in FIG. 12. Shorter sprouting times allow more batches per airlift tank. One batch of sprouting takes four days. In one year up to 90 batches can be produces. A short period of time in appropriate contrition is beneficial when an unstable recombinant protein is produced. The potential for large-scale accumulation of stable proteins in a short period also exists. For example, natural Rubisco protein accumulates to high levels within 96 hours after the onset of germination.

Sprout size can be regulated with auxins and cytokines. By adding such grown regulator to the sprouting medium, root and hypocotyl extension can be decreased without affecting cotyledon growth. The advantage of the strategy is that the spouts are smaller and more can be grown in same volume. Gibberelic acid (GA) is used in malting to synchronize the initiation of germination. Seed germination in our system is well synchronized even without GA. Addition of GA into the medium did not produce any significant benefit.

Potassium nitrate ($KNO_3$) increased the growth rate of sprouts (FIG. 12) and led to higher levels of recombinant HSA-expression (FIG. 13). Germination became uneven and was slowed down if 20 mM $KNO_3$ was added at the beginning of the process, but when nitrogen was added 6 h after beginning of germination there were no negative effects on the sprouting rate. The effect of spout size was clear. Differenced were visible after 50 h of treatment. After 96 h of treatment the average weight of a sprout treated with $KNO_3$ is more than twice that of a spout grown in unsubstituted water.

Example 8

Yield Estimates

According to FAO statistics, the average field harvest of oilseed rape in Europe is 2500 kg $ha^{-1}$ and based on our experiments 3000 kg/ha yields can be obtained in green house conditions. This translates into an annual harvest potential of 9000 kg/ha based on the fact that three harvests can be obtained in a year. Because the total protein content of a rapeseed is 25% dry weight, the total protein production level would be 2250 kg in one hectar of greenhouse space per year. If the recombinant protein of interest was expressed at the level of 5% total protein production yield would be 112.5 kg per year.

Example 9

Protein Expression in Transgenic Seeds

A construct comprising GUS gene coding region was linked to the Rubisco promoter rbcS-4A and transformed into an oilseed rape plant using *Agrobacterium* mediated transformation. Transgenic plants were grown in greenhouse until seeds were produced. Seeds of transgenic plants were allowed to sprout in 20° C. aerated water; 24° C. aerated 20 mM $KNO_3$ water or in 30° C. aerated water. After variable times of cultivation expressed GUS protein was isolated from the sprouts by homogenization in appropriate buffer and centrifugations. Specific GUS activity was determined by spectrophotometer. GUS activity per sprout was highest after 72 hours of cultivation using $KNO_3$ in the growth medium.

Protein expression of transgenic *Camelina sativa* and tobacco seeds carrying HSA under the control of rbcS-2 or rbcS-4 were also analyzed. Similarly, plants carrying tandem construct of RbcS-2-HSA were analyzed. Protein expression was analyzed from sprouts that germinated at constant light and 24° C. temperature for four days. Plants carrying a tandem construct had higher expression levels of the protein than plants carrying single construct. Furthermore, it is evident that protein expression is higher under rbcs-4 promoter than under rbcS-2 promoter. The tandem construct having two rbcS-2-HSA constructs is an example of a multiple construct according to the present invention and one skilled in the art would be able to transform plants with more than two constructs in tandem as well. Similarly, one skilled in the art would be able to use tandem constructs having rbcS-4 as the driving promoter to obtain higher protein contents.

Transgenic *Camelina* and tobacco seeds harboring rbcS-2-GUS, RbcS-4-GUS, RbcS-2-TNFR-Fc-56UTRshort, RbcS-2-TNFR-FcKDEL-56UTRshort, RbcS-4-TNFR-Fc-56UTRlong, or RbcS-4-TNFR-FcKDEL-56UTRlong constructs were obtained and analyzed further. The results are shown in FIGS. 14 and 15. Determination of GUS-activity demonstrates that enzyme activity level in rbcS-2 (rbcS-4)-GUS transgenic seeds is higher than in seeds carrying conventional 35S-GUS construct used here as positive control. Northern data is available for some TNFR-Fc-harboring *Camelina* and tobacco plants as is shown in FIG. 15.

What is claimed is:

1. A process based on a source-sink principle for converting storage reserves in transgenic dicotyledonous seeds to a composition comprising one or more desired gene products, said process comprising steps of:
    a) cultivating a transgenic dicotyledonous plant having an expression system inducible during germination, said expression system comprising one or more DNA sequences encoding one or more gene products of interest, said DNA sequences being operably linked to promoter sequences and said promoter sequence having their highest expression in cotyledons of germinating seeds;
    b) harvesting seeds of the transgenic plants
    c) germinating the transgenic dicotyledonous seeds in confined conditions, during which germination the expression system is induced and the storage reserves are mobilized;
    d) harnessing the expression system integrated in the plant genome for de novo synthesis of one or more of desired heterologous proteins from the storage reserves mobilized in step (c);
    e) inhibiting protein synthesis in the chloroplast by adding antibiotics to the germination media;
    f) stopping the germination before de novo synthesis declines; and
    g) recovering the composition.

2. The process according to claim 1, wherein the promoter is a Rubisco promoter.

3. The process according to claim 2, wherein the promoter is coded by a nucleotide sequence selected from the group consisting of SEQ ID NO:1, SEQ ID NO:2 and SEQ ID NO:3.

4. The process according to claim 1, wherein step d) comprises inhibition of endogenous Rubisco genes during sprouting.

5. The process according to claim 4, wherein 100 mg/l streptomycin is added 48 to 50 hours after initiation of germination.

6. The process according to claim 1, wherein the transgenic seeds of step b) are sterilized and the germination is performed under confined conditions providing a substantially sterile source-sink production system.

7. The process according to claim 6, wherein the germination is performed in an airlift tank.

8. The process according to claim 1, wherein the promoter is substantially silent when cultivating the transgenic plant in field conditions.

9. The process according to claim 1, wherein the germination is stopped by heating, drying, crushing, separating, extracting, pressing or filtering and subsequently recovering with or without down-stream processing methods at least one of the heterologous proteins.

10. The process according to claim 1, wherein the plant is *Brassica* species or *Camelina sativa*.

11. The process according to claim 1, wherein the heterologous protein is selected from a group consisting of HSA, and TNFR.

12. A process based on a source-sink principle for converting storage reserves in transgenic dicotyledonous seeds to a composition comprising one or more desired gene products, said process comprising steps of:
    a) cultivating a transgenic dicotyledonous plant having an expression system inducible during germination, said expression system comprising one or more DNA sequences encoding one or more gene products of interest, said DNA sequences being operably linked to promoter sequences selected from the group consisting of SEQ ID NO:1, SEQ ID NO:2 and SEQ ID NO:3;
    b) harvesting seeds of the transgenic plants;
    c) germinating the transgenic dicotyledonous seeds in confined conditions, during which germination the expression system is induced and the storage reserves are mobilized;
    d) inhibiting endogenous Rubisco genes by adding streptomycin after initiation of germination, whereby the expression system integrated in the plant genome is harnessed for de novo synthesis of one or more of desired heterologous proteins from the storage reserves mobilized in step (c);
    e) stopping the germination before de novo synthesis declines; and
    f) recovering the composition.

13. The process according to claim 12, wherein the germination is performed in an air lift tank.

14. The process according to claim 12, wherein the plant is *Brassica* species or *Camelina sativa* plant.

15. The process according to claim 12, wherein the heterologous protein is selected from a group consisting of HSA, and TNFR.

16. A process based on a source-sink principle for converting storage reserves in transgenic dicotyledonous seeds to a composition comprising one or more desired gene products, said process comprising steps of:
    a) germinating transgenic dicotyledonous seeds in confined conditions, wherein said seeds comprise an expression system inducible during germination, said expression system comprising one or more DNA sequences encoding one or more gene products of interest, said DNA sequences being operably linked to promoter sequences and said promoter sequence having their highest expression in cotyledons of germinating seeds, during which germination the expression system is induced and the storage reserves are mobilized;
    b) harnessing the expression system integrated in the plant genome for de novo synthesis of one or more of desired heterologous proteins from the storage reserves mobilized in step (a);
    c) inhibiting protein synthesis in the chloroplast by adding antibiotics to the germination media;
    d) stopping the germination before de novo synthesis declines; and
    e) recovering the composition.

* * * * *

SEQUENCE LISTING

<160> NUMBER OF SEQ ID NOS: 24

<210> SEQ ID NO 1
<211> LENGTH: 2175
<212> TYPE: DNA

<213> ORGANISM: Brassica rapa (campestris)
<220> FEATURE:
<221> NAME/KEY: misc_feature
<222> LOCATION: (1)..(2175)
<223> OTHER INFORMATION: RbcS-4A

<400> SEQUENCE: 1

| | | | | | |
|---|---|---|---|---|---|
| gtttcctgag | tgttgcacct | cctcagtctg | agccgtatta | agttcaaacc | aaactgccgc | 60 |
| ttctgctcta | gctttactca | ggactgaaac | cgaggagtag | tgtatcttct | caaaagccag | 120 |
| accatttctc | gccttccata | gatgccagag | tatccaagga | aaaacatcg | tatcgctatc | 180 |
| ttttggagac | ttcctactca | tttccaggag | atgatataaa | cctgccaccg | ggagtttgat | 240 |
| cgaggacctt | tcccaagtgt | ccttcgccat | ggggcaagaa | aaagtagat | ggcagatcga | 300 |
| ttcaatacca | ccattacata | ctttgcaagc | agagtctact | tgaatacctc | tactacgaag | 360 |
| acgttccatg | accgctaaag | ccccagagag | agctttccaa | aggaaatgct | taattttttgg | 420 |
| aggagcacgg | atcttccaca | gagatttcca | aaggtatttc | tccaggggag | aagagaagt | 480 |
| tgaaatgcta | ccatcttcct | caggaagcga | atcgacaaat | ctttaaccac | tccgtgatgt | 540 |
| gtagattcca | tcttttgtga | agccccactt | ataaccatct | tcctgcatcc | tatttggctt | 600 |
| caagcgaagg | atgatctcag | catcatgatc | agtaaacgtt | cttctcacaa | gagctgcatc | 660 |
| ccaggcagaa | gagttaggga | gcagcaggtc | tgagattgtc | agcgtcagat | caatgacact | 720 |
| atcctgtctg | tagttaggag | tcctcggtat | agggtcgata | atccaattca | cgtgccacac | 780 |
| attagaactc | ctaccattac | caatgtctct | aatcaaacct | ttgctcagca | gctctctacc | 840 |
| atgtaaaatg | cttcgccatg | catatgacgg | cctcgaacct | aaactgcttt | gcaagaagtc | 900 |
| attgtttgca | aagtatctac | ttttgaggat | tcgagccacc | agagagttgg | ggttattcat | 960 |
| gatcctccat | gcttgcttag | ccaagaaagt | taagattagt | gataacgatc | agctagcgaa | 1020 |
| gaaagttaag | attagtgatt | agaactacg | aatcacctgt | cacatttagc | tggcctttc | 1080 |
| tgtattctaa | tatttttaa | aatgaaatta | tcaacagaaa | aaagatattt | taaattctta | 1140 |
| ataaaatgaa | attattttc | tgacccgctc | tggccttgac | ctctataaat | atttgagccg | 1200 |
| gtgctatgtt | caaagttctt | ttcggtcagc | ttgcgtctgc | atagtgcata | tgatggaagg | 1260 |
| atttttttggt | ggtacatgct | ctcggcggtg | tagaagcttg | cagaagagtt | gatgaaattt | 1320 |
| gagtcatcac | tagcggattc | agtgacggta | atgaggtgat | gacgtagctg | aaccaattac | 1380 |
| gcgtgacatt | tcgtagggag | acgcgtattg | gtgatataaa | ttcttaaaac | tacaagtgtt | 1440 |
| agagtatgtt | taatagggag | ttcttaaggt | gtggttctta | gaacatgatt | atcgatggtg | 1500 |
| ggaggagggt | ttttacgcgt | ggaccccctcc | atcttttgc | aaacaccgtg | tttcaatgtc | 1560 |
| cccaaataaa | aaatgtttca | cagaggtttg | ttgtactgtt | tatggatctc | acagacacgt | 1620 |
| agcgacttgc | gattcatttt | tttttttttt | tttttttaaat | ttaagaaacc | caaaagtgtt | 1680 |
| tttaccgata | atcatgctct | tagttcttag | cgttttttagt | taaaagttaa | aagacagatt | 1740 |
| tttatattcc | gttaaaaatc | cttcattaag | cctgcagtaa | ttttctttt | tgtgtgcaac | 1800 |
| tacaagtggt | agcaaattaa | tgtaactttc | tttcacggcg | ttgattgttg | ggccgattat | 1860 |
| gtaccacacg | atctcatcct | tatgggctct | acgaaaagtt | gacccacgaa | ataaggaag | 1920 |
| gagcctaaag | catcggctca | agtggagacc | agaccagtaa | ccatacgttt | tcataatacg | 1980 |
| ataagataag | ataacgtttc | tgtcacgtgg | cattttcatt | gtggtcaagt | atcgagataa | 2040 |
| gggtatcaac | accgttcata | atcctgtggc | tgttaacgac | gatatcatga | atatccata | 2100 |
| agggttctca | ctctatatag | atgaccaaag | caatagacta | acagtaagag | ttaagagaag | 2160 |

```
gaagaagaag tagtc                                              2175
```

<210> SEQ ID NO 2
<211> LENGTH: 1016
<212> TYPE: DNA
<213> ORGANISM: Brassica rapa (campestris)
<220> FEATURE:
<221> NAME/KEY: misc_feature
<222> LOCATION: (1)..(1016)
<223> OTHER INFORMATION: RbcS-4B

<400> SEQUENCE: 2

```
aacccgaacc gaatccgatc cgataaaaat gaatccgaac cgatccgaat ccgacataaa    60
taccgaatgg atcctgtttt ttggtatttt gggttatggg tattatccga accgaacccg   120
gacctaaatg gatatccgat agaacccgaa acatttaaaa tcacaaaaag aacttctacc   180
aaatatgatc ataattctta atatgtatcc aaaatacttt aagatattat tgaacttcta   240
aaataattat atgttacatg aaggttgatg gtggaatgtg gcggttgatg cctgaagttt   300
ttaggttttg gttttgtttt tattgaataa tgtttctcat ttcatgagaa cttatttttt   360
gttttatgat ttcatttatc tggttttctt tctatcacta actatgttta tattttgctt   420
gattttgaat gatcacgttt gatgttttt cttatttttg aatcgatttt acttatgttt   480
tggctattaa aatatgtaca aatcatgtat tttaaattcg aagaaccgat ttcatttatg   540
ttttagttac aaaataggta caaatcagat atttttaaac caagaaccg attgggaccc   600 gaacccgaaa gtacaatgag ttataccggt tctttgaaga tttactaacc ccgacccgaa   660
cccgatagaa cccgaaccgg tcccgaaccg aacttttata taacccgaat ggggttgatt   720
ttgataaacc cgaaaaccg aaacccgaat ggataaaacc gaaacccgat tgggaccccg   780
aatgcccatg cctaccagta accatgcgtt ttcataatac gataagataa gataacgttt   840
ctgtcacgtg gcattttcat tgtggtcaag tatcgagata agggtatcaa caccgttcat   900
attcctgtgg ctgttaacga cgatatcatg aaatatccat aagggttctc actctatata   960
gatgaccaaa gcaatagact aacagtaaga gttaagagaa ggaagaagaa gtagtc      1016
```

<210> SEQ ID NO 3
<211> LENGTH: 1651
<212> TYPE: DNA
<213> ORGANISM: Brassica rapa (campestris)
<220> FEATURE:
<221> NAME/KEY: misc_feature
<222> LOCATION: (1)..(1651)
<223> OTHER INFORMATION: RbcS-2

<400> SEQUENCE: 3

```
ccctttttccg tcataagttt tatatatata aaaacatatt tgcccttctt atctccctca    60
tctctctctc tctctctctc tctctctctc tctctctctc tctctccctc              120
tctctctctc tctctctctc tcatccggcg agtgtaaaca tatataacta ttaaattaat   180
ttagaaaaca aactgtttaa tatagccaaa atgaacgtg gggttttagt tgtaaaacaa   240
aaaaaccata ctaactcaaa tctgaacaca ccgtatttt cttgatgttg aattaccact   300
tgatttgtca attttaccaa aggatcccct caaaattgta actcaaatgt aatacattat   360
acatcaaaaa gtaactcaaa aatctaaaaa ctaatcttac atttaaccca aacttaatct   420
tataacacat tgcttttaat gtaagtatga tttttttggat taataacttt tacattcatt   480
aaaaaaatca taaaaaatac aacactatct gaccagagct aaatataatt tgtaatcttg   540
```

-continued

```
tatcattgcg atagaggcat ccgaaatttc atttaattga gaagttcggt tcggttcagc   600
atgtttataa aaaaaatggt ttttggctcg ttctgttcgg taatcggtta gatcggtttc   660
aaaaaaaatt tgttcccaaa tttcaatccg aactaaccta gctaaccaaa acttcgaatc   720
gaagtaacca agctacctaa aattactcaa aattttgaac cgaactaaca gaattaacca   780
aaacattgga ccgaattaac caattttacc caaattttta accgaaatat aatcagaacc   840
aaaaacttaa gttagtttcg gtaaaatttt aaaaactgaa ctacccaaat accaaactga   900
actgaatttt tttatgttc gacaagattt tagtcgaacc gaactacctg aatccgcagg   960
aagttaccca tcacagagag atgcacaaag cattacctaa aaacgttaca tttagtgttt  1020
tggtaccact tttattgatt ttttttttg acagctattg atttagttta tagtttttaa  1080
ctattaagta acagtttgtt tttcgtgtca aaaaaaaag taacagtttt tatacggttt  1140
tacttttaac ttaccaatcg gacccactat tcttttgttt ttgttggttt gaatatggac  1200
atgaccatta cagtagtatc attactcata gttaattag tacgacatac atgtataatt  1260
caagtacatc tcgtatagta atttcaattg tgaatttaat aatgaaccta atcaaattaa  1320
gcgaaactaa ttcatataaa tagaaggtcc gcgaacattg aaatgtagat catgcgtcag  1380
aattgtcctc tctcagtagg aaggagccaa aagcattggc tcaagttgag acgagtaacc  1440
atacacattc atacgttttc ttacaagata agataagata atgttatttc tcacccttc   1500 tttaatacct gtggcagtta acgacgatat catgaaatca tgatccttcg atcattaggg  1560
ctttatacct cttgcgcttc tcactatata tagataacca aagcaatagg caaacaagta  1620
agttaagaga aagaagaag aagaagtagt a                                  1651
```

```
<210> SEQ ID NO 4
<211> LENGTH: 42
<212> TYPE: DNA
<213> ORGANISM: artificial sequence
<220> FEATURE:
<223> OTHER INFORMATION: primer e3a

<400> SEQUENCE: 4
caucaucauc aucaaccgtc aagtccagtg catcagtttc at                      42

<210> SEQ ID NO 5
<211> LENGTH: 27
<212> TYPE: DNA
<213> ORGANISM: artificial sequence
<220> FEATURE:
<223> OTHER INFORMATION: primer atu

<400> SEQUENCE: 5
cuacuacuac uattttttttt ttttttt                                     27

<210> SEQ ID NO 6
<211> LENGTH: 48
<212> TYPE: DNA
<213> ORGANISM: artificial sequence
<220> FEATURE:
<223> OTHER INFORMATION: adapter

<400> SEQUENCE: 6
gtaatacgac tcactatagg gcacgcgtgg tcgacggccc gggctggt               48

<210> SEQ ID NO 7
<211> LENGTH: 8
<212> TYPE: DNA
<213> ORGANISM: artificial sequence
```

```
<220> FEATURE:
<223> OTHER INFORMATION: adapter

<400> SEQUENCE: 7 accagccc                                                                    8

<210> SEQ ID NO 8
<211> LENGTH: 22
<212> TYPE: DNA
<213> ORGANISM: artificial sequence
<220> FEATURE:
<223> OTHER INFORMATION: adapter primer AP1

<400> SEQUENCE: 8
gtaatacgac tcactatagg gc                                                   22

<210> SEQ ID NO 9
<211> LENGTH: 34
<212> TYPE: DNA
<213> ORGANISM: artificial sequence
<220> FEATURE:
<223> OTHER INFORMATION: UTR2-specific L1 primer

<400> SEQUENCE: 9
ggccacactt gacaatccga tataacatgc ctca                                      34

<210> SEQ ID NO 10
<211> LENGTH: 19
<212> TYPE: DNA
<213> ORGANISM: artificial sequence
<220> FEATURE:
<223> OTHER INFORMATION: AP2 primer

<400> SEQUENCE: 10
actatagggc acgcgtggt                                                       19

<210> SEQ ID NO 11
<211> LENGTH: 23
<212> TYPE: DNA
<213> ORGANISM: artificial sequence
<220> FEATURE:
<223> OTHER INFORMATION: UTR2-specific L2 primer

<400> SEQUENCE: 11
caaatggaaa tgaaatgagg tag                                                  23

<210> SEQ ID NO 12
<211> LENGTH: 30
<212> TYPE: DNA
<213> ORGANISM: artificial sequence
<220> FEATURE:
<223> OTHER INFORMATION: RbcS-RN

<400> SEQUENCE: 12
acccgggccc aggagagcat agaggaagcc                                           30

<210> SEQ ID NO 13
<211> LENGTH: 30
<212> TYPE: DNA
<213> ORGANISM: artificial sequence
<220> FEATURE:
<223> OTHER INFORMATION: RbcS-R1

<400> SEQUENCE: 13
ctgtgaatgg agcaaccatg gccgcttgag                                           30
```

<210> SEQ ID NO 14
<211> LENGTH: 30
<212> TYPE: DNA
<213> ORGANISM: artificial sequence
<220> FEATURE:
<223> OTHER INFORMATION: RbcS-R2

<400> SEQUENCE: 14

```
ctgtgaatgg agcaaccatg gccgcttgag                                      30
```

<210> SEQ ID NO 15
<211> LENGTH: 2132
<212> TYPE: DNA
<213> ORGANISM: artificial sequence
<220> FEATURE:
<223> OTHER INFORMATION: codon-optimized Human Serum Albumin (HSA) gene

<400> SEQUENCE: 15

```
aagcttgaag acgacatgaa gtgggttact ttcatctctc ttcttttcct tttctcttct     60
gcttactctg atgctcataa gtctgaagtt gctcatagat tcaaagatct cggagaggag    120
aacttcaagg ctcttgttct tatcgctttc gctcagtacc ttcagcagtg ccctttcgag    180
gatcatgtta agctcgttaa cgaggttaca gagttcgcta agacttgcgt tgctgatgag    240
tcggccgaga actgcgataa gtctcttcat actcttttcg gagataagct ctgcactgtt    300
gctactctta gagagactta cggagagatg gctgattgct gcgctaagca ggagcctgag    360
agaaacgagt gcttccttca acataaggat gataacccta accttcctag acttgttaga    420
cctgaggttg acgtcatgtg cactgctttc catgataacg aggagacttt cctcaagaag    480
tacctttacg agatcgctag aaggcatcct tacttctacg ctcctgagct tctttttcttc    540
gctaagagat acaaggctgc tttcactgag tgctgccagg ctgctgataa ggctgcatgc    600
cttcttccta gctcgatga gcttagagat gagggaaagg cttcttctgc taagcagaga    660
ctcaagtgcg ctagccttca gaagttcgga gagagagctt caaggcttg ggctgttgct    720
agactttctc agagattccc taaggctgaa ttcgctgaag tttctaagct cgttactgat    780
cttactaagg ttcacactga gtgctgccat ggtgatcttc ttgagtgcgc tgatgataga    840
gctgatcttc taagtacat ctgcgagaac caggattcta tctcttctaa acttaaggag    900
tgctgcgaga agcctcttct tgagaagtct cattgcatcg ctgaggttga aacgatgag    960
atgcctgctg atcttccttc tcttgctgca gacttcgttg agtctaagga tgtttgcaag   1020
aactacgctg aggctaagga tgttttcctt ggaatgttcc tttacgagta cgctagaagg   1080
catcctgatt actctgttgt tcttcttttg agcttgcta agacttacga gactactctc   1140
gagaagtgct gcgctgctgc tgatcctcat gagtgctacg ctaaggtttt cgatgagttc   1200
aagccactag tcgaggagcc tcagaacctt atcaagcaga actgcgagct tttcaagcag   1260
cttggagagt acaagttcca gaacgctctt cttgttagat acactaagaa ggttccacaa   1320
gtttctactc ctactcttgt tgaggtttca agaaaccttg gaaaagttgg atctaagtgc   1380
tgcaagcatc ctgaggctaa gagaatgcct tgcgctgagg attacctttc tgttgttctt   1440
aaccagcttt gcgttcttca tgagaaaaca ccggtgtctg atagagttac taagtgctgc   1500
actgagtctc ttgttaacag aaggccttgc ttctctgctc ttgaagttga tgaaacgtac   1560
gttcctaagg agttcaacgc tgagactttc actttccatg ctgatatctg cactctttct   1620
gagaaggaga gacagatcaa gaagcagact gctcttgttg agcttgttaa gcataagcct   1680
aaggctacta aggagcaatt gaaggctgtt atggatgatt cgctgctttt cgttgagaag   1740
```

```
tgctgcaagg ctgatgataa ggagacttgc ttcgctgagg agggaaagaa gctcgttgct      1800
gcttctcagg ctgctcttgg actttaagag ctcttcgctt tcatctaata atatcttctc      1860
atttcatttc caataagtct gtttcttttt ttctcttttgg atttctgtta cgagactttc     1920
tatatcggat tgtaaaatgt ctgattttat gaacatgtaa tttctatatt gcttcttcgt      1980
cttggttact ttccgatggc tattaggttt tcaactctta tgggataag aagccagtca       2040 aaataactta acaaaacagg ttagataatg ttagtggtat attgtagaat aagaaaagca      2100
gcaaacagca gtggtgacct ctagaaggat cc                                    2132
```

<210> SEQ ID NO 16
<211> LENGTH: 714
<212> TYPE: DNA
<213> ORGANISM: artificial sequence
<220> FEATURE:
<223> OTHER INFORMATION: light chaing (anti-hevein 1C2) coding region
<220> FEATURE:
<221> NAME/KEY: misc_feature
<222> LOCATION: (1)..(66)
<223> OTHER INFORMATION: sequence coding for mouse signal peptide
<220> FEATURE:
<221> NAME/KEY: misc_feature
<222> LOCATION: (67)..(324)
<223> OTHER INFORMATION: light chain antihevein 1C2 antigen variable
    region
<220> FEATURE:
<221> NAME/KEY: misc_feature
<222> LOCATION: (325)..(714)
<223> OTHER INFORMATION: kappa light chain constant region
<400> SEQUENCE: 16

```
atggattttc aagtgcagat tttcagcttc ctgctaatca gtgcctcagt cataatatcc      60
agaggagaaa cgacactcac gcagtctcca tcctccctgt ctgcatctgt aggagacaga      120
gtcaccatca cttgccgggc aagtcagagc attagcagct atttaaattg gtatcagcag      180
aaaccaggga agcccctaa gctcctgatc tatgctgcat ccagtttgca aagtggggtc       240
ccatcaaggt tcagtggcag tggatctggg acagatttca ctctcaccat cagcagtctg      300
caacctgaag attttgcaac ttactactgt caacagagtt acagtacccc tcggacgttc      360
ggccaaggga cacgactgga gattaaacgt cgaactgtgg ctgcaccatc tgtcttcatc      420
ttcccgccat ctgatgagca gttgaaatct ggaactgcct ctgttgtgtg cctgctgaat      480
aacttctatc ccagagaggc caaagtacag tggaaggtgg ataacgccct ccaatcgggt      540
aactcccagg agagtgtcac agagcaggac agcaaggaca gcacctacag cctcagcagc      600
accctgacgc tgagcaaagc agactacgag aaacacaaag tctacgcctg cgaagtcacc      660
catcagggcc tgagctcgcc cgtcacaaag agcttcaaca ggggagagtg ttga            714
```

<210> SEQ ID NO 17
<211> LENGTH: 498
<212> TYPE: DNA
<213> ORGANISM: Brassica rapa (campestris)
<220> FEATURE:
<221> NAME/KEY: terminator
<222> LOCATION: (1)..(498)
<223> OTHER INFORMATION: rbcS-4 terminator
<400> SEQUENCE: 17

```
ttcgctttca tataataata tcttctcatt tcatttccaa taagtctgtt tcttttttc      60 tctttggatt tctgttacga gactttctat atcggattgt aaaatgtctg attttatgaa      120
catgtaattt ctatattgtt cttcttcgt ggttactact ttcagatggc tattaggttt      180
```

```
tcaatttatt gggataagaa aacagtcaga ataataactt tacaaaactg gttagataag      240
gttagtggta atatttttt agaataggaa acattactac ctacggaaaa aaattcatac      300
gaagttaatt agttcatcaa agattcaaat aacaagcaca gttataaaag aaacaagcat      360
tgtatcattt catcgtcaca ttgacataga tttcaagcat acagtagtag tcatcatttg      420
atatttgatg tttcacactc atcatatgca gtttctgaga tcgtatacat actattggtg      480
cattataatt gcaaataa                                                   498

<210> SEQ ID NO 18
<211> LENGTH: 1434
<212> TYPE: DNA
<213> ORGANISM: artificial sequence
<220> FEATURE:
<223> OTHER INFORMATION: heavy chain (anti-hevein 1C2) coding region
<220> FEATURE:
<221> NAME/KEY: misc_feature
<222> LOCATION: (1)..(57)
<223> OTHER INFORMATION: a sequence coding for mouse signal peptide
<220> FEATURE:
<221> NAME/KEY: misc_feature
<222> LOCATION: (58)..(387)
<223> OTHER INFORMATION: heavy chain anti-hevein 1C2 antigen variable
      region
<220> FEATURE:
<221> NAME/KEY: misc_feature
<222> LOCATION: (445)..(990)
<223> OTHER INFORMATION: igG heavy chain constant region
<220> FEATURE:
<221> NAME/KEY: misc_feature
<222> LOCATION: (445)..(990)
<223> OTHER INFORMATION: IgG1 heavy chain constant region

<400> SEQUENCE: 18
atggaatgga gttggatatt tctctttctc ctgtcaggaa ctgcaggtgt ccactctcag       60
atcaccttga aggagtctgg tcctacgctg gtgaaaccca cacagaccct cacgctgacc      120
tgtaacctct ctgggttctc gctcagcacc agcggagtgg gtgtgggctg gatccgtcag      180
cccccaggaa aggccctgga gtggctcgca ctcatttatt gggatgatga taagcgctac      240
agtccatctc tgaggaacag actcaccatc accaaggaca catccaaaaa ccaggtggtc      300
cttacaatga ccaacatgga ccctgtggac acaggcacat atttctgtgc acgcagtgtc      360
aattatgatg acgtttcggg gacttatcac agccacaact ggttcgaccc ctggggccag      420
ggaaccctgg tcaccgtctc ctcatccacc aagggcccat cggtcttccc cctggcaccc      480
tcctccaaga gcacctctgg gggcacagcg gccctgggct gcctggtcaa ggactacttc      540
cccgaaccgg tgacggtgtc gtggaactca ggcgccctga ccagcggcgt gcacaccttc      600
ccggctgtcc tacagtcctc aggactctac tccctcagca gcgtggtgac cgtgccctcc      660
agcagcttgg gcacccagac ctacatctgc aacgtgaatc acaagcccag caacaccaag      720
gtggacaaga gagttgagcc caaatcttgt gacaaaactc acacatgccc accgtgccca      780
gcacctgaac tcctgggggg accgtcagtc ttcctcttcc ccccaaaacc caaggacacc      840
ctcatgatct cccggacccc tgaggtcaca tgcgtggtgg tggacgtgag ccacgaagac      900
cctgaggtca agttcaactg gtacgtggac ggcgtggagg tgcataatgc caagacaaag      960
ccgcgggagg agcagtacaa cagcacgtac cgtgtggtca gcgtcctcac cgtcctgcac     1020
caggactggc tgaatggcaa ggagtacaag tgcaaggtct ccaacaaagc cctcccagcc     1080
cccatcgaga aaaccatctc caaagccaaa gggcagcccc gagaaccaca ggtgtacacc     1140
ctgcccccat cccgggagga gatgaccaag aaccaggtca gcctgacctg cctggtcaaa     1200
```

```
ggcttctatc ccagcgacat cgccgtggag tgggagagca atgggcagcc ggagaacaac    1260
tacaagacca cgcctcccgt gctggactcc gacggctcct tcttcctcta tagcaagctc    1320
accgtggaca agagcaggtg gcagcagggg aacgtcttct catgctccgt gatgcatgag    1380
gctctgcaca accactacac gcagaagagc ctctccctgt ccccgggtaa atga          1434

<210> SEQ ID NO 19
<211> LENGTH: 558
<212> TYPE: DNA
<213> ORGANISM: artificial sequence
<220> FEATURE:
<223> OTHER INFORMATION: signal sequence and TNFR
<220> FEATURE:
<221> NAME/KEY: misc_feature
<222> LOCATION: (1)..(69)
<223> OTHER INFORMATION: signal sequence
<220> FEATURE:
<221> NAME/KEY: misc_feature
<222> LOCATION: (70)..(489)
<223> OTHER INFORMATION: TNFR sequence

<400> SEQUENCE: 19
atggcgcccg tcgccgtctg ggccgcgctg gccgtcggac tggagctctg ggctgcggcg    60
cacgccttgc ccgcccaggt ggcatttaca ccctacgccc cggagcccgg gagcacatgc    120
cggctcagag aatactatga ccagacagct cagatgtgct gcagcaaatg ctcgccgggc    180
caacatgcaa aagtcttctg taccaagacc tcggacaccg tgtgtgactc ctgtgaggac    240
agcacataca cccagctctg gaactgggtt cccgagtgct tgagctgtgg ctcccgctgt    300
agctctgacc aggtggaaac tcaagcctgc actcgggaac agaaccgcat ctgcacctgc    360
aggcccggct ggtactgcgc gctgagcaag caggagggg gccggctgtg cgcgccgctg    420
cgcaagtgcc gcccgggctt cggcgtggcc agaccaggaa ctgaaacatc agacgtggtg    480
tgcaagccct gtcccgggg gacgttctcc aacacgactt catccacgga tatttgcagg    540
ccccaccaga tctgtgag                                                  558

<210> SEQ ID NO 20
<211> LENGTH: 576
<212> TYPE: DNA
<213> ORGANISM: artificial sequence
<220> FEATURE:
<223> OTHER INFORMATION: Arabidobsis VSP1 (vegetative storage protein)
      and a part of rbcS-4 terminator
<220> FEATURE:
<221> NAME/KEY: misc_feature
<222> LOCATION: (1)..(226)
<223> OTHER INFORMATION: Arabidopsis VSP1
<220> FEATURE:
<221> NAME/KEY: misc_feature
<222> LOCATION: (227)..(576)
<223> OTHER INFORMATION: a part of rbcS-4 terminator

<400> SEQUENCE: 20
ttaagcatct atcttcatgg cattgtcccc ttgtatccat ttcatatcta tgtcgtttcg    60
tttatctttg tagccgtttt ggcaccactg cttaaataaa atgccaatcc tatcataact    120
caataagtac aacgacttcg tactaaattt tgttttttcgt taagggatc attaatcaag    180 tttccatgaa atgatgaaca tgtaatttct atattgtttc ttcttcgtgg ttactacttt    240
cagatggcta ttaggttttc aatttattgg gataagaaaa cagtcagaat aataacttta    300
caaaactggt tagataaggt tagtggtaat atttttttag aataggaaac attactacct    360
acggaaaaaa attcatacga agttaattag ttcatcaaag attcaaataa caagcacagt    420
```

```
tataaaagaa acaagcattg tatcatttca tcgtcacatt gacatagatt tcaagcatac    480
agtagtagtc atcatttgat atttgatgtt tcacactcat catatgcagt ttctgagatc    540
gtatacatac tattggtgca ttataattgc aaataa                              576
```

```
<210> SEQ ID NO 21
<211> LENGTH: 1149
<212> TYPE: DNA
<213> ORGANISM: Brassica rapa (campestris)
<220> FEATURE:
<221> NAME/KEY: misc_feature
<222> LOCATION: (1)..(1149)
<223> OTHER INFORMATION: rbcS-1

<400> SEQUENCE: 21
```

```
ctggtaattc tgttttaata acactgtcat gaaaactgaa ttcataggtt tctccaggcc    60
gtagatagtg gaagcctaga tcgtcgtcgt tagatataca attaatcttc aagatattgt    120
ttcgaccaag agagttctta aagtgcacgg agttttttc attccacttt gcgttactca     180
aacctatgca caatccaata gtgagaagaa acacgagag acgattcatt gtgttgatta    240
tttgtaatgg ccttcttcta tagttctttt aaatttagaa gtaatccgta gataaccaag    300
agggaagatg tgtaatatat atatatatag tggcgttaca cggataagca ctcattttt     360 ctctattttt aaacatcttt gttttgacta atattaagaa aacgttgatc gcttttacta    420
tttttcgtgt ccttatcccg tgttgctgtt ttgcatctat ttaaagagta gatgctatag    480
tttttttacg gcttagacta gatgcttttg gtaatttgtt tcagtgttca gctttgaccc    540 ccttttttg gtgtaaatgt taaaattcag ccttcagctt tgacctttgt gatattatat    600
gaatgactgt gtttatgtaa aatttattga tttataaaac tcttaagaaa aactatatta    660
ataaaaaata gaattgttac tcttcttcgt ttgagtatga acataatcat caatagtgct    720
ctcatcactc ataagttata actaatgacg acattacatg tctgattcaa gtaatttaat    780
tttcttgtag tacaggtcca cgaagattta aatgtaggtc atgcgtctca tttcttttct    840
gccaaaagga aggagccaag agaatcggct caagtggaca ctagtaacca tacacattca    900
ctcattacct tccaagaaaa gataagataa gaaaattttc tgccacgtgg ccttatcata    960
gtggtctgta tcgataaggg tgtcaacacc tttccttaat cctgtggcag gtaacgacgt   1020
tatcatcaga catgaatccc gcactctttg atctaagggc tttatgcctc atgccgtcct   1080
cactatatat agatgaccaa aggaatagac aaacaagtaa gtaagagaaa agagaaaaaa   1140
gaagtagta                                                           1149
```

```
<210> SEQ ID NO 22
<211> LENGTH: 877
<212> TYPE: DNA
<213> ORGANISM: Brassica rapa (campestris)
<220> FEATURE:
<221> NAME/KEY: misc_feature
<222> LOCATION: (1)..(877)
<223> OTHER INFORMATION: RbcS-3

<400> SEQUENCE: 22
```

```
ctggtgattc tattttaata gattaaatat tattctttag aagacgaagc atgagatcga    60
tgacaacgca atgctcattt catctggttt ttctgtcctt gcctcaattg gttactgtta    120
cagatgttaa taaatgagta attaccaata ggatacccta agttttttcca aactttcaaa   180 cccaaaactt actctatttg acttaagagc atttctaaga gcaatgttac ttttagagca    240
```

-continued

```
tttctaagag caatgttact tttaaagttt agtgaacttt aaatttgagg tttaagagca      300
tgtccaatgg ttagaagaca gacttacagt ttaactaccg tgttcagtta ccaatcgggc      360
ccactatata atattgtttc ccttcttcgt ttatcgacgt tagcattaac agtgtactcc      420
ttgctcacaa ctaagtagct cataacttgt aatagttata atactaaatg tgatcttatt      480
aattaactga atcaaactaa gccaatagtt aggagttcca ctaacattaa agagtaggcc      540
atgtgtttga tttgtcgtct cccaatagga aggaaccaaa agcatcggct caagtggagg      600
ccagcagtaa atcagtaacc atatatacac acattcatac attttaatgc aagataagat      660
aatagcattt ctgccacgtg gccttaacat agtggtcagt atcgataagg gtctcaacac      720
ctttctttaa tcatgtggca gttaacgacg ttatcatgaa atctggaccc tctggttatt      780
agggcctttt cctcttgcgg ttctcgttat atatagataa ccaaagcgat agacaaacaa      840
gtaagttaag agaaaagaag aagaagaaga agtagta                              877
```

<210> SEQ ID NO 23
<211> LENGTH: 904
<212> TYPE: DNA
<213> ORGANISM: Brassica rapa (cmapestris)
<220> FEATURE:
<221> NAME/KEY: misc_feature
<222> LOCATION: (1)..(904)
<223> OTHER INFORMATION: RbcS-5

<400> SEQUENCE: 23

```
gtcgacaaaa ctcttctttt atgtcgcagg atggtccgaa tgagacaata acaccttcca       60
tccttctgat gaggtcacat attcaatcat gtcagttaaa gtcacatatc catgcgatgc      120
gaatgcagct tgcttcgtct caatgtatta aatacgaatc agactgtatt gttcctactt      180
gatgacagag tcaacatact tttcccaaag catgggcgtg acgtcgtcac gtagatcgca      240
ttattgtctt ttatcatata atgaaccggg ctacctttat ctttgggttt ttgaatttgt      300
tgggctcttt atagaatcgg atcgggcatt gatgagagtg tgaagtccac ctccaacaaa      360
aactcttgaa ctaaactaa tgatgtcctt gtattattag tgataacttt tctaagtaat      420
gtattgtgga aaattacatg tttgattcaa atcattttct tattaataat taaatattga      480
ttgagaacta actaaccgaa tcgatgtaca tgccaaactg aatcttacac aattgaacat      540
aagttcaaac cattaaaagt aggtcaggtt ctgattcttt tttcaattgg aaggagtcaa      600
aagcatgact caagtggaca ccagtaacca tacacattca ctcattccct cacaagaaac      660
gataagataa tggaattttc tgccacgtgg ccttatcata gtggtctgta ttgataaggg      720
tgtcaacacc tttccttaat cctgtggcag gcaacgacgt tatcatgaat cttggaccca      780
tttattacta gggcttttg tctcttgccg ttctcactat ataagatga ccaaagcaat       840 agacaagcaa gtaaagaaa ggagaaaaag aagaagaaga agaagagaag aactagtaca      900
cgta                                                                  904
```

<210> SEQ ID NO 24
<211> LENGTH: 12
<212> TYPE: DNA
<213> ORGANISM: artificial sequence
<220> FEATURE:
<223> OTHER INFORMATION: KDEL signal; chemically synthesized

<400> SEQUENCE: 24

```
aaagacgagc tg                                                          12
```